US006579695B1

(12) United States Patent
Lambalot et al.

(10) Patent No.: US 6,579,695 B1
(45) Date of Patent: Jun. 17, 2003

(54) PHOSPHOPANTETHEINYL TRANSFERASES AND USES THEREOF

(75) Inventors: Ralph H. Lambalot, Wrentham, MA (US); Amy M. Gehring, Beulah, MI (US); Ralph Reid, San Francisco, CA (US); Christopher T. Walsh, Wellesley, MA (US)

(73) Assignees: President and Fellows of Harvard College, Cambridge, MA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 08/728,742

(22) Filed: Oct. 11, 1996

Related U.S. Application Data

(60) Provisional application No. 60/005,152, filed on Oct. 13, 1995, and provisional application No. 60/021,650, filed on Jul. 12, 1996.

(51) Int. Cl.[7] .......................... C12P 19/26; C12P 21/02; C12N 9/10; C07H 21/04
(52) U.S. Cl. ...................... 435/41; 435/69.1; 435/193; 435/68.1; 536/23.2; 536/23.7
(58) Field of Search ............................... 435/193, 69.1, 435/71.1, 41, 43, 130, 76, 71.3; 536/23.2, 23.7

(56) References Cited

U.S. PATENT DOCUMENTS 5,824,513 A  10/1998  Katz et al. ................. 435/76

FOREIGN PATENT DOCUMENTS

| CA | 2100791 | 7/1993 |
| WO | WO 93/13663 | 7/1993 |

OTHER PUBLICATIONS

Ratner et al., Biotechnology, vol 7, no 11, pp. 1129–1133, Nov. 1989.*
Plunkett (Oct. 23, 1995) GenBank accession AAA79825.*
Lambalot et al. A new enzyme superfamily—the phosphopantetheinyl transferases. Chem Biol. Nov. 1, 1996 vol. 3, No. 11, pp.: 923–936.*
Werkmeister et al. Coenzyme A: fatty acid synthetase apoenzyme 4'–phosphopantetheine transferase in yeast. Biochem Biophys Res Commun. Sep. 16, 1980, vol. 96, No. 1, 483–90.*
Gehring et al. Enterobactin biosynthesis in *Escherichia coli*: isochorismate lyase (EntB) is a bifunctional enzyme that is phosphopantetheinylated by EntD and then acylated by EntE using ATP and 2,3–dihydroxybenzoate. Biochemistry. Jul. 15, 1997, vol. 36, pp. 8495–8503.*
George et al, "Current methods in sequence comparison and analysis," in Macromolecular Sequencing and Synthesis, Selected Methods and Applications, 1988, D.H. Schlesinger (ed.), Alan R. Liss, Inc., New York, NY, pp. 127–149.*

Barton, "Protein sequence alignment and database scanning," in Protein Structure Prediction, A Practical Approach, 1996 IRL Press at Oxford University Press, Oxford, UK, pp. 31–63.*
Armstrong S. K. et al., "The *Escherichia coli* enterobactin biosynthesis gene, entD: nucleotide sequence and membrane localization of its protein product", *Molecular Microbiology*, vol. 3(6) pp. 757–766 (1989).
Baldwin, Jack E. et al., "Isolation and Partial Characterisation of ACV Synthetase from *Cephalosporium acremonium* and *Streptomyces clavuligerus*: Evidence for the Presence of Phophopantothenate in ACV Synthease", *The Journal of Antibiotics*, vol. 44 No. 2 pp. 241–248 (1991).
Billich, Andrea et al., "Enzymatic Synthesis of Cyclosporin A*", *The Journal of Biological Chemistry*, vol. 262 No. 36 pp 17258–17259 (1987).
Borchet, Stefan et al., "Induction of Surfactin Production in *Bacillus subtilis* by gsp, a Gene Located Upstream of the Gramicidin S Operon in *Bacillus brevis*", *Journal of Bacteriology*, vol. 176 No. 8 pp. 2458–2462 (1994).
Coderre, Peter E. et al., "The entD Gene of the *Escherichia coli* K12 Enterobactin Gene Cluster", *Journal of General Microbiology*, vol. 135 pp. 3042–3055 (1989).
Cosmina, Paola et al., "Sequence and anlysis of the genetic locus responsible for surfactin synthesis in *Bacillus subtilis*", *Molecular Microbiology*, vol. 8(5) pp. 821–831 (1993).
Elhussein, Salah A. et al., "Plant holo–(acyl carrier protein) synthase", *Biochemistry Journal*, vol. 252 pp. 39–45 (1988).
Elovson, John et al., "Acyl Carrier Protein", *The Journal of Biological Chemistry*, vol. 243 No. 13 pp. 3603–3611 (1968).
Fischl, Anthony S. et al., "Isolation and Properties of Acyl Carrier Protein Phosphodiesterase of *Escherichia coli*", *Journal of Bacteriology*, vol. 172 No. 9 pp. 5445–5449 (1990).
Geiger, Otto et al., "Isolation of the *Rhizobium leguminosarum* NodF Nodulation Protein: NodF carries a 4'–Phosphopantetheine Prosthetic Group" *Journal of Bacteriology*, vol. 173 No. 9 pp. 2872–2878 (1991).

(List continued on next page.)

*Primary Examiner*—Elizabeth Slobodyansky
(74) *Attorney, Agent, or Firm*—Lahive & Cockfield, LLP

(57) ABSTRACT

The invention pertains to isolated phosphopantetheinyl transferases, such as the *E. coli* acyl carrier protein synthase, which transfer a phosphopantetheinyl group onto a substrate. The enzyme can be purified from a natural source, produced recombinantly, or synthetically. Accordingly, the invention provides compositions and kits including phosphopantetheinyl transferases and host cells expressing phosphopantetheinyl transferases. The invention also provides nucleic acids encoding phosphopantetheinyl transferases and vectors comprising such nucleic acids. The invention further provides methods for phosphopantetheinylating a substrate in vitro or in vivo and methods for producing antibiotics in vitro or in vivo.

3 Claims, 17 Drawing Sheets

OTHER PUBLICATIONS

Gerngross, T. U. et al., "Overexpression and Purification of the Soluble Polyhydroxyalkanoate Synthase from *Alcaligenes eutrophus*: Evidence for a Required Posttranslational Modification for Catalytic Activity", *Biochemistry*, vol. 33 No. 31 pp. 9311–9320 (1994).

Grossman, Trudy H., et al., "Isolation and Characterization of *Bacillus subtilis* Genes Involved in Siderophore Biosynthesis: Relationship between *B. subtilis sfp°* and *Escherichia coli* entD Genes", *Journal of Bacteriology*, vol. 175 No. 19 pp. 6203–6211 (1993).

Heaton, Michael P. et al., "Role of the D–Alanyl Carrier Protein in the Biosynthesis of D–Alanyl–Lipoteichoic Acid", *Journal of Bacteriology*, vol. 176 No. 3 pp. 681–690 (1994).

Holak, Tadeusz A. et al., "Three–dimensional structure of acyl carrier protein in solution determined by nuclear magnetic resonance and the combined use of dynamical simulated annealing and distance geometry", *European Journal of Biochem.*, vol. 175 pp. 9–15 (1988).

Issartel, Jean–Paul et al., "Activation of *Escherichia coli* prohaemolysin to the mature toxin by acyl carrier protein–dependent fatty acylation"*Nature*, vol. 351 pp. 759–761 (1991).

Jackowski, Suzanne et al., "Metabolism of 4'-Phosphopantetheine in *Escherichia coli*", *Journal of Bacteriology*, vol. 158 No. 1 pp. 115–120 (1984).

Jones, Lesley A. et al., "The cloning an overexpression of *E Coli* acyl carrier protein (ACP)", *Biochemical Society Transactions*, vol. 21 pp. 202S (1993).

Kleinkauf, H. et al., "Biosynthesis of Peptide Antibiotics", *Annual Review Microbiology*, vol. 41 pp. 259–289 (1987).

Kleinkauf, H. et al., "Nonribosomal biosynthesis of peptide antibiotics", *European Journal of Biochem.*, vol. 192 pp. 1–15 (1990).

Lam, Hon–Ming et al., "Suppression of Insertions in the Complex pdxJ Operon of *Escherichia coli* K–12 by Ion and Other Mutations", *Journal of Bacteriology*, vol. 174 No. 5 pp, 1554–1567 (1992).

Lawen, Alfons et al., "Cell–Free Biosynthesis of New Cyclosporins", *The Journal of Antibiotics*, vol. 42 No. 8 pp. 1283–1289 (1989).

Lawen, Alfons et al., "Cyclosporin Synthetase", *The Journal of Biological Chemistry*, vol. 265 No. 19 pp. 11355–11360 (1990).

Majerus, Phillip W. et al., "Acyl Carrier Protein, IV. The Identification of 4'–Phosphopantetheine as the Prosthetic Group of the Acyl Carrier Protein", *P.N.A.S.*, vol. 53 pp. 410–417 (1965).

Nakano, Michiko M. et al., "Identification of a Genetic Locus Required for Biosynthesis of the Lipopeptide Antibiotic Surfactin in *Bacillus subtilis*", *Journal of Bacteriology*, vol. 170 No. 12 pp. 5662–5668 (1988).

Nakano, Michiko M. et al., "Isolation and characterization of sfp: a gene that functions in the production of the lipopeptide biosurfactant, surfactin, in *Bacillus subtilis*", *Mol. Gen. Genet.* vol. 232 pp. 313–321 (1992).

Nakano, Michiko M. et al., "Cloning and Characterization of srfB, a Regulatory Gene Involved in Surfactin Production and Competence in *Bacillus subtilis*", *Journal of Bacteriology*, vol. 171 No. 10 pp. 5347–5353 (1989).

Perego, Marta et al., "Incorporation of D–Alanine into Lipoteichoic Acid and Wall Teichoic Acid in *Bacillus subtilis*", *The Journal of Biological Chemistry*, vol. 270 No. 26 pp. 15598–15606 (1995).

Polacco, Mary L. et al., "A Mutant of *Escherichia coli* Conditionally Defective in the Synthesis of Holo–[Acyl Carrier Protein]*", *The Journal of Biological Chemistry*, vol. 256 No. 11 pp. 5750–5754 (1981).

Rawlings, Merriann et al., "The Gene Encoding *Escherichia coli* Acyl Carrier Protein Lies within a Cluster of Fatty Acid Biosynthetic Genes*", *The Journal of Biological Chemistry*, vol. 267 No. 9 pp. 5751–5754 (1992).

Rock, Charles O. et al., "Acyl Carrier Protein fron *Escherichia coli**", *Methods in Enzymology*, vol. 71 pp. 341–351 (1981).

Rusnak, Frank et al., "Biosynthesis of the *Escherichia coli* Siderophore Enterobactin: Sequence of the entF Gene, Expression and Purification of EntF, and Analysis of Covalent Phosphopanteteine", *Biochemistry*, vol. 30 No. 11 pp. 2916–2927 (1991).

Shen, Ben et al., "Purification and Characterization of the Acyl Carrier Protein of the *Streptomyces glaucescens* Tetracenomycin C Polyketide Synthase", *Journal of Bacteriology*, vol. 174 No. 11 pp. 3818–3821 (1992).

Sofia, Heidi J. et al., "Analysis of the *Escherichia coli* genome V. DNA sequence of the region from 76.0 to 81.5 minutes", *Nucleic Acids Research*, vol. 22 No. 13 pp. 2576–2586 (1994).

Stein, Torsten et al., "Gramicidin S Synthetase 1 )Pheylalanine Racemase), a Prototype of Amino Acid Racemases Containing the Cofactor 4"–Phosphopantetheine", *Biochemistry*, vol. 34 pp. 4633–4642 (1995).

Takiff, Howard E. et al., "Locating Essential *Escherichia coli* Genes by Using Mini–Tn10 Transposons: the pdxJ Operon", *Journal of Bacteriology*, vol. 174 No. 5 pp. 1544–1553 (1992).

Ullrich, Christian et al., "Cell–Free Biosynthesis of Surfactin, a Cyclic Lipopeptide Produced by *Bacillus subtilis*", *Biochemisstry*, vol. 30 pp. 6503–6508 (1991).

Black, T. et al., "Analysis of a Het⁻ Mutation in *Anabaena sp.* Strain PCC 7120 Implicates a Secondary Metabolite in the Regulation of Heterocyst Spacing", *Journal of Bacteriology*, vol. 176 (8), pp. 2282–2292 (1994).

Borell, C. et al., "Cloning and biochemical characterization of LYS5 gene of *Saccharomyces cerevisiae*", *Current Genet.*, vol. 23, pp. 299–304 (1988).

Burton, D. et al., "Interconversion of Apo– and Holofatty Acid Synthetases of Rat and Pigeon Liver", *Methods in Enzymology*, vol. 62, pp. 249–262 (1979).

Ford, R. et al., "Physical and functional characterization of the cloned lys1+ gene of *Schizosaccharomyces pombe*", *J. Basic Microbiol.*, vol. 33, pp. 179–186 (1993).

Jackowski, S. et al., "Ratio of Active to Inactive Forms of Acyl Carrier Protein in *Escherichia coli**", *The Journal of Biological Chemistry*, vol. 258 (24), pp. 15186–15191 (1983).

Miller, K. et al., "The LYS5 gene of *Saccharomyces cerevisiae*", *Gene*, vol. 172 (1), pp. 167–168 (1996).

Prescott, D. et al., "Acyl Carrier Protein", *The Journal of Biological Chemistry*, vol. 244 (16), pp. 4517–4521 (1969).

Prescott, D. et al., "Acyl Carrier Protein", *Adv. Enzymol Relat. Areas Mol Biol*, vol. 36, pp. 269–311 (1972).

Prescott, D. et al., "Acyl Carrier Protein Synthetase", *Methods Enzymol.*, vol. 35, pp. 95–101 (1975).

Powell, G. et al., "Acyl Carrier Protein", *The Journal of Biological Chemistry*, vol. 244 (20), pp. 5616–5624 (1969).

Rajnarayan, S. et al., "Physical and Biochemical characterization of the cloned LYS5 gene reguired for α–aminoadipate reductase activity in the lysine biosynthetic pathway of *Saccharomyces cerevisiae*", *Current Genet.*, vol. 2, (1), pp. 13–16 (1992).

Rutkoski, A. et al. "Fatty Acid Synthetase from Chloroplasts of Soybean Cotyledons: ACP Activation and CoA Inhibition", *Biochemical and Biophysical Research Communications*, vol. 84 (2), pp. 428–434 (1978).

Storts, D. et al., "Properties of Revertants of Lys2 and Lys 5 Mutants as well as α–Aminoadipate–Semialdehyde Dehydrogenase from *Saccharomyces Cerevisiae*", *Biochemical and Biophysical Research Communications*, vol. 161 (1), pp. 182–186 (1989).

Tsuge, K. et al., "Isolation of a gene essential for biosynthesis of the lipopeptide antibiotics plipastatin B1 and surfactin in *Bacillus subtilis* YB8", *Arch Microbiol*, vol. 165, pp. 243–251 (1996).

Fernandez et al., "Acyl carrier protein import into chloroplasts. Both the presursor and mature forms are substrates for phosphopantetheine attachment by a soluble chloroplast holo–acyl carrier protein synthase," *J. Biol. Chem.* 266(11);7220–6 (1991).

Savage et al., "Phosphopantethenylated precursor acly carrier protein is imported into spinach (spinacia oleracea) chloroplasts," *Plant Physiol.* 104:989–995 (1994).

* cited by examiner

Fig. 2
2A
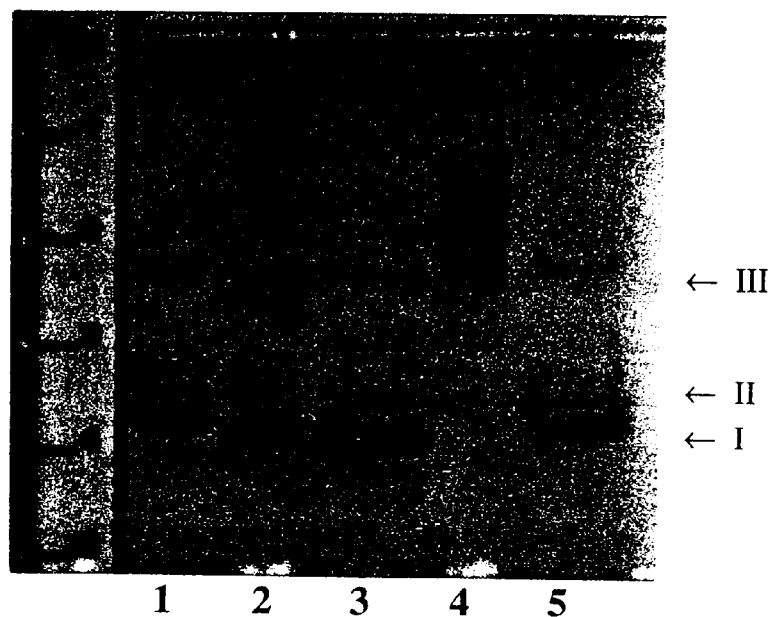
1  2  3  4  5
← III
← II
← I
2B
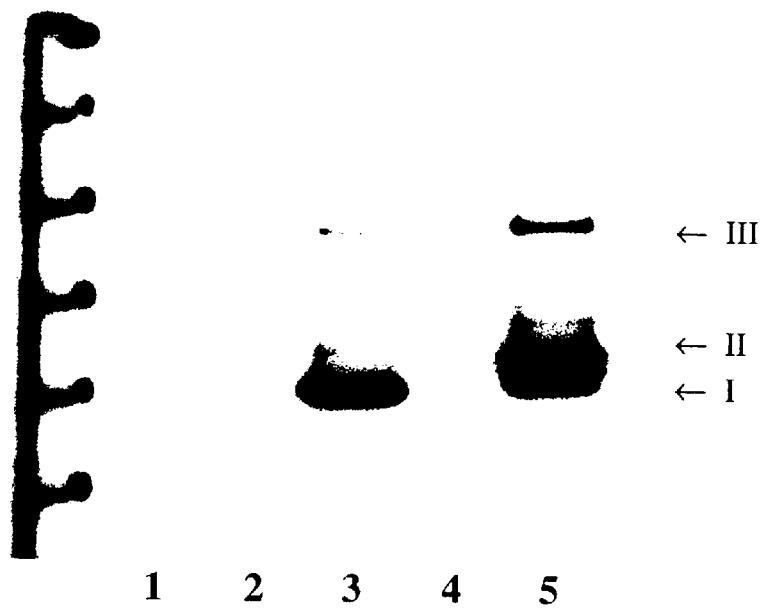
1  2  3  4  5
← III
← II
← I

```
100  N - V N I S I S H D D F Q A T A V A L - S - E F    canal_fas2_cterm.pep
100  D - V K V S I S H D D L Q A V A V A V - S T K K    yeast_fas2_cterm.pep
101  Q - V S V S I S H D S Q A V A V A V - S - Q F      penpa_fas2_cterm.pep
102  S - V S V S I S H D D N Q S V A L - A - H K        S_pombe_acps.pep
103  N - I Q L S L S Y G D D C V V A V A L - G V R K W C L W P L    E_nidulans_fas
100  Y K C S C C S L F S S V T N L S I T K L Q V Q E L C N L F L    B_brev_hyp_acps
105  E Y K L A V C A A H P D F C D - G I E M K T Y E E L - L        B_subtilis_lpa_acps
105  G Y K M A V C A A H P D F P E - D I T M V S Y E E L - L        B_subtilis_sfp_acps
97   E K I V I T L C Q H D                                          entD_acps
106  N - M H V T L A D E R H Y A C A T V I I E S                    acps.pep
```

Fig. 8

```
  2  - - - - A I L G L G T D I V E I A R T E A V I A R S G D R L A R R V L S D N E W A I W K T H H Q P   acpS E. coli
  1  - - - - S R Q P I G I D I E E I F S V Q T A R E L T D N I I T P A E H E R L - - - A D C G L A F     entD E. coli
  1  V I G A F D S Q P I G I D I E K T K P I S L - E I A K R F F S K T E Y S D L L A K D K D E Q T D Y   sfp B. subtilis
  1  - - - - S N H P V G I D I E R I S E I D I - K I A E Q F F H E N E Y I W L Q S K A Q N S Q V S S     gsp B. brevis
  2  - - - - - - G G V G V D V E L I T S I N V E - - N D T F I E R N F T P Q E I E Y C S A Q P S V       fas2 S. cerevisiae 47  V R F L A K R F A V K E A A A K A F - - - N Q F E V F N D E L G K P R                             acpS E. coli
 42  S L A L T L A F S A K E S A F K A S E I Q T D A G F L D Y Q I I S W N K Q Q V I H R E N - - - -    entD E. coli
 49  F Y H L - - - W S M K E S F I K Q E G K G L S L P L D S F S V R L H Q D G Q V S I E L P D S H S P C sfp B. subtilis
 44  F F E L - - - W T I K E S Y I K A I G K G M Y I P I N S F W I D K N Q T - Q T V I Y K Q N K K E P - gsp B. brevis
 41  Q S S F A G T W S A K E A V F K S L G V K S L G G G A A L - - - - K D I E I V R V N K N A P A       fas2 S. cerevisiae 89  - L R L W G E A L K L A E K L G V A N M H V T L A D - - E R H Y A C A T V I I E S                   acpS E. coli
 87  - - - - E M F A - - - - - - - V H W Q I K E K I V I T L C Q H D                                   entD E. coli
 96  Y I K T Y E V D - - P G Y K M A V C A A H P D F P E - D I T M V S Y E E                             sfp B. subtilis
 89  - V T I Y E P E L F E G Y K C S C C S L F S S V T N L S I T K L Q V Q E L C N L F                   gsp B. brevis
 84  - V E L H G N A K K A A E E A G V T D V K V S I S H - - D - D L Q A V A V S T                       fas2 S. cerevisiae
```

PHOSPHOPANTETHEINYL TRANSFERASES AND USES THEREOF

RELATED APPLICATIONS

This application claims the benefit of U.S. provisional application Serial No. 60/005,152, filed Oct. 13, 1995 entitled "Acyl Carrier Protein Synthases and Uses Thereof" and U.S. provisional application Serial Number 60/021,650, filed Jul. 12, 1996 entitled "Acyl Carrier Protein Synthases and Uses Thereof". The contents of each of these applications is incorporated herein by reference.

GOVERNMENT SUPPORT

Work described herein was supported in part by NIH grants GM20011 and GM16583-02. The U.S. government therefore may have certain rights in this invention.

BACKGROUND OF THE INVENTION

Acyl carrier protein (ACP) is a small acidic protein (8,800 Da) responsible for acyl group activation in fatty acid biosynthesis. The gene encoding ACP (acpP) has been cloned and overexpressed (Rawlings, M. and Cronan, J. E., Jr. (1992) *J. Biol. Chem.*, 267, 5751–5754; Jones, A. L., et al. (1993) *Biochem. Soc. Trans.*, 21, 202S) and the solution structure of ACP has been solved by NMR spectroscopy (Holak, T. et al. (1988) *Eur. J. Biochem.* 175:9–15). Homologs of *E. coli* ACP exist throughout nature in two forms; either as an integral domain of a much larger multifunctional enzyme (type I) or as a discrete protein capable of associating with several other enzymes constituting a multienzyme synthase complex (type II). In these two forms, ACPs play central roles in a broad range of other biosynthetic pathways that depend on iterative acyl transfer steps, including polyketide (Shen, B., et al. (1992) *J. Bacteriol.* 174:3818–3821), non-ribosomal peptide (Baldwin, J. E., et al. (1991) *J. Antibiot.* 44:241–247), and depsipeptide biosynthesis (Rusnak, F., et al. (1991) *Biochemistry* 30:2916–2927) as well as in the transacylation of oligosaccharides (Geiger, O., et al. (1991) *J. Bacteriol.* 173:2872–2878) and proteins (Issartel, J. P., et al. (1991) *Nature* 351:759–761).

A definitive feature of ACP is the 4'-phosphopantetheine (4'-PP) prosthetic group (Majerus, P. W. et al. (1965) *Proc. Natl. Acad. Sci. USA* 53:410–417). 4'-PP is attached through a phosphodiester linkage to a conserved serine residue found in all ACPs. Acyl groups of the many substrates recognized by type I and type II ACPs are activated for acyl transfer through a thioester linkage to the terminal cysteamine thiol of the 4'-PP moiety. The β-alanyl and pantothenate portions of the 4'-PP structure are believed to serve as a tether between the phosphodiester-ACP linkage and the terminal thioester, suggesting that 4'-PP may function as a swinging arm, shuttling growing acyl chains between various active sites, e.g. as in the sequential addition of 11 amino acids by the 800 kDa cyclosporin synthetase (Lawen, A. and Zocher, R. (1990) *J. Biol. Chem.* 265:11355–11360).

Holo-ACP synthase (holo-ACPS) transfers the 4'-PP moiety from Coenzyme A (CoA) to Ser-36 of apo-ACP to produce holo-ACP and 3',5'-ADP in a $Mg^{2+}$ dependent reaction. The (acyl carrier synthase protein) ACPS from *E. coli* was partially purified 780-fold from crude extracts (Elovson, J. and Vagelos, P. R. (1968) *J. Biol. Chem.* 243:3603–3611), and the ACPS from spinach has been partially purified (Elhussein, S. A., et al. (1988) *Biochem. J.* 252:39–45), but remarkably little has been shown about the mechanism or specificity of this post-translational phosphopantetheinylation process. A mutant of *E. coli* conditionally defective in the synthesis of holo-ACP has been identified and the mutant phenotype attributed to an altered holo-ACP synthase activity (Polacco, M. L. and Cronan, J. E., Jr. (1981) *J. Biol. Chem.* 256:5750–5754).

SUMMARY OF THE INVENTION

This invention pertains to isolated and purified natural and recombinant phosphopantetheinyl transferases, e.g., acyl carrier protein synthases (ACPSs), from eukaryotes, prokaryotes, or plants. Also within the scope of the invention are active fragments of phosphopantetheinyl transferases, modified phosphopantetheinyl transferases, and modified active fragments of phosphopantetheinyl transferases. These forms of phosphopantetheinyl transferase are preferably purified to at least about 60% purity, more preferably to at least about 70% purity, more preferably to at least about 80% purity, more preferably to at least about 90% purity and even more preferably to at least about 95% purity. The phosphopantetheinyl transferase of the invention can be used for in vitro phosphopantetheinylation of substrates, such as acyl carrier proteins (ACPs), which have, for example, been produced by overexpression in a host cell. Kits including the phosphopantetheinyl transferase described herein are also within the scope of the invention.

The invention also provides host cells modified to express at least one nucleic acid encoding at least one phosphopantetheinyl transferase or active fragment thereof. In one embodiment, the host cells of the invention are further modified to express at least one nucleic acid encoding at least one substrate of a phosphopantetheinyl transferase. Such host cells may further express nucleic acids encoding other components associated with the ACP. Modified host cells of the invention can be used for the production of antibiotics or other compounds whose synthesis requires an ACP.

BRIEF DESCRIPTION OF THE DRAWINGS

FIG. 2 Panel A shows the results of a native SDS-PAGE analysis showing in vitro formation of holo-ACP using recombinant ACPS (Lane 1, apo-ACP; lane 2, holo-ACP standard (Sigma), reduced with DTT; lane 3, $^3$H-labeled holo-ACP formed in vitro using recombinant ACPS, reduced with DTT; lane 4, holo-ACP standard, not reduced with DTT; lane 5, $^3$H-labeled holo-ACP formed in vitro using recombinant ACPS, not reduced with DTT).

FIG. 2 Panel B represents an autoradiogram of the gel shown in FIG. 2 Panel A which confirms the introduction of [$^3$H]phosphopantetheine into holo-ACP (I), holo-ACP-CoA mixed disulfide (II), and (holo-ACP)$_2$ disulfide (III).

FIG. 6 represents an alignment of amino acid sequences of yeast fatty acid synthases Fas 2 (SEQ ID NOS:1–5), Gsp (SEQ ID NO:6), Lpa (SEQ ID NO:7), Sfp (SEQ ID NO:8), EntD (SEQ ID NO:9), and E. coli ACPS(SEQ ID NO:10). Conserved residues are boxed and indicated by stars.

FIG. 8 represents an alignment of amino acid sequences of E. coli ACPS, entD, sfp, gsp, and the yeast fatty acid synthase fas2 (SEQ ID NO:11) showing the amino acid sequence homology between these proteins. The two areas showing the strongest homology are boxed and shaded.

FIG. 9 Panel B shows amino acid sequence alignments of the consensus sequences of the P-pant transferase enzyme superfamily. Highly conserved residues are boxed.

FIG. 14 Panel B is a diagram representing the amount of Holo-ACP formed as a function of time upon incubation of Apo-ACP with EntD, ACPS, or o195.

DETAILED DESCRIPTION OF THE INVENTION

Figure 1:
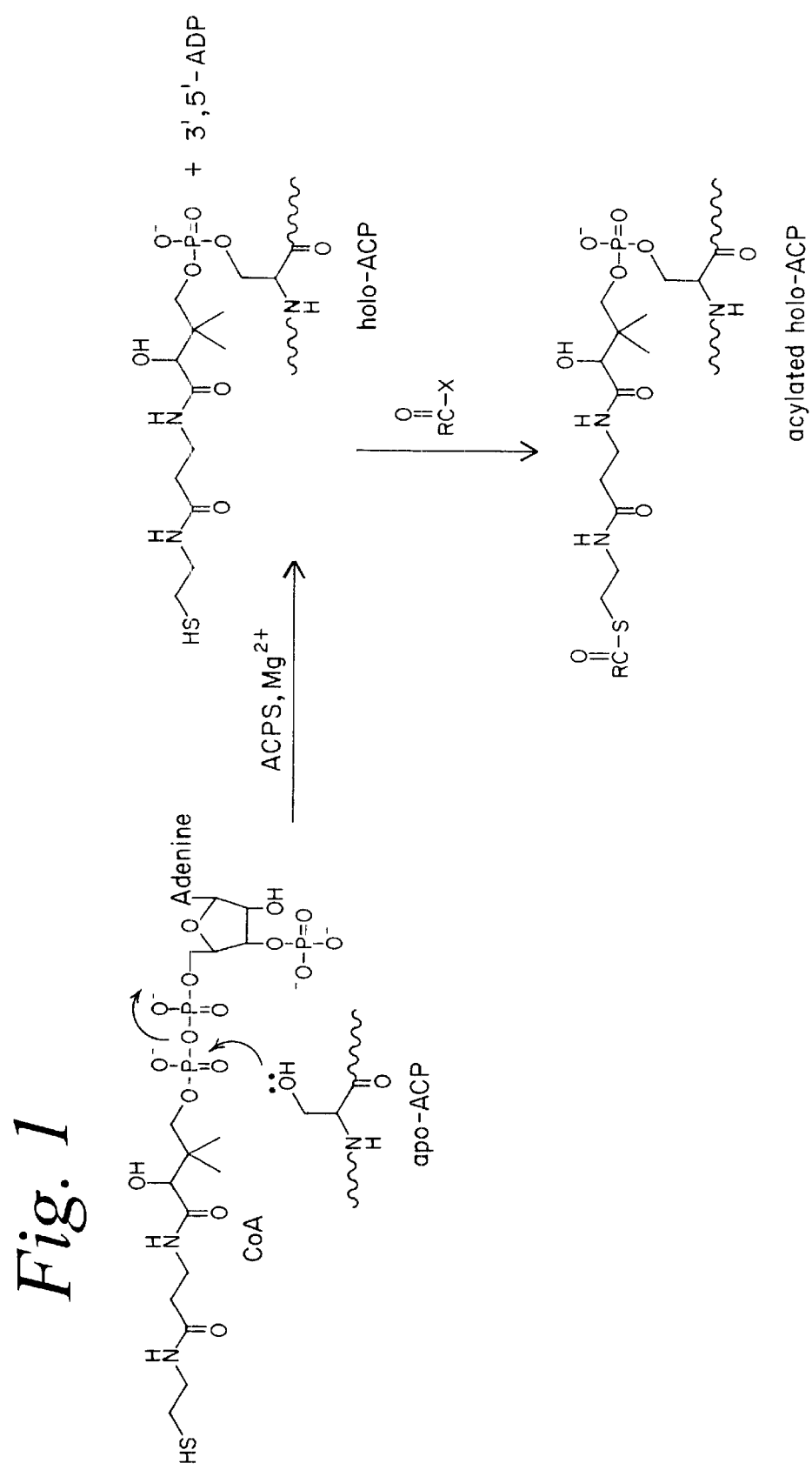
FIG. 1 is a schematic representation of the transfer of a 4'-PP moiety from CoA to Ser-36 of apo-ACP by ACPS to produce holo-ACP and 3',5'-ADP in a $Mg^{2+}$ dependent reaction. Holo-ACP can then activate acyl groups for acyl transfer through a thioester linkage to the terminal cysteamine of the 4'-PP moiety.

This invention provides isolated and purified phosphopantetheinlyating enzymes, also termed phosphopantetheinyl transferases, such as acyl carrier protein synthases (ACPS) or active fragments thereof. The term "phosphopantetheinyl transferase" and "phosphopantetheinyl transferase enzyme" and "phosphopantetheinylating enzyme" is intended to include a molecule, e.g. enzyme, which catalyzes the transfer of a 4'-phosphopantetheine group from a donor compound, such as CoA, to a substrate. Accordingly, phosphopantetheinyl transferases include natural enzymes, recombinant enzymes, or synthetic enzymes, or active fragments thereof, which are capable or phosphopantetheinylating a compound. Preferred phosphopantetheinyl transferases include enzymes, such as the E. coli ACPS, which modify acyl carrier proteins (ACPs) and preferably result in activation of an ACP. The term phosphopantetheinyl transferase also includes enzymes which modify non-acyl carrier proteins, which require a 4'-phosphopantetheine group, for example, for enzymatic activity. The terms "isolated" and "purified" are used interchangeably herein and refer to a phosphopantetheinyl transferase or active fragment thereof that is substantially free of other components of the host organism with which it is associated in its natural state. The terms "isolated" and "purified" are also used to refer to a phosphopantetheinyl transferase or active fragment that is substantially free of cellular material or culture medium when produced by recombinant DNA techniques, or chemical precursors or other chemicals when chemically synthesized.

In one embodiment, the phosphopantetheinyl transferase or active fragment thereof is purified from a cell naturally expressing the synthase, such as a procaryotic or eucaryotic cell. Since ACPs are involved in fatty acid biosynthesis, it is likely that all species having fatty acids would require phosphopantetheinyl transferases for their synthesis. Procaryotic cells which produce phosphopantetheinyl transferase include bacteria, such as E. coli. Phosphopantetheinyl transferases can also be isolated from eucaryotic cells, for example mammalian cells, yeast cells, and insect cells. Other sources for phosphopantetheinylating enzymes include plant tissues, such as spinach and pea leaves (Elhussein, et al. supra).

Purification of a phosphopantetheinyl transferase from a cell naturally expressing the enzyme can be accomplished using standard techniques. However, it is preferred that the process of purification of a phosphopantetheinyl transferase from a native source include an affinity purification step over an apo-acyl carrier protein column, such as is further detailed in the Exemplification Section. Use of this affinity purification step allows purification of a phosphopantetheinyl transferase to at least about 60% purity, more preferably to at least about 70% purity, and most preferably to at least about 80% purity. Purification of a phosphopantetheinyl transferase to at least about 90% purity, 95% purity, 97% purity, 98% purity or 99% purity by this technique is preferred. In addition, purification of a phosphopantetheinyl transferase from a natural source by the techniques described herein will preferably result in an enrichment of the phosphopantetheinyl transferase by at least about 800 fold or 1,000 fold, more preferably at least about 10,000 fold, more preferably at least about 50,000 fold, and even more preferably at least about 70,000 fold. It is also preferred that a purified phosphopantetheinyl transferase have a specific activity of about 250 mU/mg, more preferably about 400 mU/mg, and even more preferably about 500 mU/mg of protein. The specific activity of a phosphopantetheinyl transferase is defined in mU/mg with one Unit being equal to 1 μmol of substrate, e.g., holo-ACP, formed per minute at 37° C. in an in vitro assay, such as described in the Exemplification section.

Another embodiment of the invention provides an isolated and purified phosphopantetheinyl transferase, such as an ACPS, or active fragment thereof produced by recombinant techniques. Recombinant phosphopantetheinyl transferase or active fragment. thereof can be produced by expression of a nucleic acid encoding the synthase or fragment thereof in an appropriate host cell. Host cell, expression vectors and techniques for expression of heterologous nucleic acids are known to those skilled in the art. For example, using recombinant techniques, a phosphopantetheinyl transferase can be expressed as an intracellular protein, a membrane associated protein, or as a secreted protein. In one embodiment of the invention, a phosphopantetheinyl transferase or active fragment thereof is expressed in a procaryotic cell, such as a bacterial cell, preferably *E. coli*. Alternatively, the phosphopantetheinyl transferase or fragment thereof can be expressed in a eukaryotic cell, such as a yeast cell, a mammalian cell, such as the CHO or COS cells, or in an insect cell (baculovirus system). The phosphopantetheinyl transferase or fragment thereof can also be expressed in a plant cell. Nucleic acid regulatory elements required for the expression of nucleic acid encoding a phosphopantetheinyl transferase or fragment thereof in the various systems, and methods for introducing one or more nucleic acids in these host cells are well known in the art. Such techniques are routine and are described, for example in Sambrook et al., (*Molecular Cloning: A Laboratory Manual,* 2nd Edition, Cold Spring Harbor Laboratory press (1989)), and other laboratory textbooks.

If a phosphopantetheinyl transferase of the invention is produced recombinantly or synthetically, it may not be necessary to purify the enzyme significantly. A recombinantly produced phosphopantetheinyl transferase may have an activity identical to that of its natural counterpart, or it may have an activity which varies more or less from that of its natural counterpart. For example, a recombinantly produced phosphopantetheinyl transferase can vary in the efficiency of catalysis. It is possible to modify the amino acid sequence of the enzyme to, e.g., improve its efficiency, or to change its substrate specificity, or both.

Using the techniques described herein, a phosphopantetheinyl transferase or active fragment thereof can be "overexpressed" in an appropriate host cell. The term "overexpression" of a phosphopantetheinyl transferase is intended to include expression of the nucleic acid encoding a phosphopantetheinyl transferase to levels which are about 100 fold higher, more preferably about 1,000 fold higher, more preferably about 10,000 fold higher, and even more preferably about 100,000 fold higher than the level of the expression of the endogenous phosphopantetheinyl transferase.

Various methods can be used for isolating and purifying recombinant phosphopantetheinyl transferase or fragment thereof from a host cell, which are preferably adapted to the specific host system used for expression. A preferred method of purification of a phosphopantetheinyl transferase or fragment thereof comprises an apo-acyl carrier protein affinity purification step. A method of purification of phosphopantetheinyl transferase including such an affinity purification step is described in the Exemplification section. Purification of a recombinant phosphopantetheinyl transferase or fragment thereof by this technique results in a preparation of phosphopantetheinyl transferase or active fragment thereof having a purity of at least about 90% or greater, preferably at least about 95% purity, more preferably at least about 97% purity, more preferably at least about 98% purity, and even more preferably at least about 99% purity. The purified recombinant phosphopantetheinyl transferase or fragment thereof preferably has a specific activity of about 200 mU/mg of protein, more preferably about 250 mU/mg of protein, and even more preferably about 300 mU/mg of protein.

This invention further pertains to isolated or purified "active fragments" of a phosphopantetheinyl transferase which are capable of phosphopantetheinylating a substrate. An "active fragment" of a phosphopantetheinyl transferase is intended to include a fragment of a phosphopantetheinyl transferase that is capable of phosphopantetheinylating a substrate. Active fragments of phosphopantetheinyl transferases are included in the term phosphopantetheinyl transferases as used herein, since active fragments of phosphopantetheinyl are capable of transfering a phosphopantetheine to a substrate. Active fragments can be produced using the techniques previously described herein for the preparation of purified phosphopantetheinyl transferase, recombinant phosphopantetheinyl transferase, or chemically synthesized using known techniques. For example, a peptide fragment of a phosphopantetheinyl transferase can be obtained by expressing nucleic acid fragments of a nucleotide sequence encoding a phosphopantetheinyl transferase in an appropriate host cell and screening the resulting peptide fragments for activity using known techniques. Various methods are known in the art to prepare libraries of clones expressing various fragments of a phosphopantetheinyl transferase. These clones can then be screened to identify those which express an active fragment capable of phosphopantetheinlyating a substrate. In one method, a fragment of a phosphopantetheinyl transferase is tested in an in vitro assay in which apo-acyl carrier protein and CoA having a radiolabelled 4'-phosphopantetheine group is incubated with the test phosphopantetheinyl transferase fragment in an appropriate buffer. The amount of radiolabel incorporated in the holo-acyl carrier protein is then measured and is representative of the activity of the fragment of the phosphopantetheinyl transferase. Further details regarding this in vitro test are provided in the Exemplification section.

Other compounds within the scope of the invention include modified phosphopantetheinyl transferase or modified active fragments thereof. The term "modification" is intended to include addition, deletion, or replacement of one or more amino acid residues in the phosphopantetheinyl transferase or active fragment thereof, such that the phosphopantetheinylating activity of the enzyme is either maintained, increased, or decreased. "Modified phosphopantetheinyl transferase" or "modified active fragment" also includes a phosphopantetheinyl transferase or fragment in which the substrate specificity has been altered. For example, a modified phosphopantetheinyl transferase or modified active fragment thereof may be capable of phosphopantetheinylating a different acyl carrier protein than the non-modified phosphopantetheinyl transferase. Alternatively, the modified phosphopantetheinyl transferase may have a different range of specificity. In particular, modification of the enzyme can result in a phosphopantetheinyl transferase capable of phosphopantetheinylating additional substrates. On the other hand, modification of a phosphopantetheinyl transferase can result in a phosphopantetheinyl transferase with a more restricted range of substrates. It is possible to determine the target(s) of a phosphopantetheinyl transferase by, for example, performing in vitro phosphopantetheinylation tests, such as described above or in the examples and replacing the *E. coli* apo-acyl carrier protein with the substrates that are of interest.

Modified phosphopantetheinyl transferases or modified active fragments thereof further include those in which the stability or solubility, or both has been altered. Other modified phosphopantetheinyl transferases include those wherein a "tag" is attached to the phosphopantetheinyl transferase or active fragment thereof, such as for facilitating purification of the protein from the host cell producing it. Such tags are well known in the art and include polypeptide recognized by specific antibodies.

This invention further provides homologs of phosphopantetheinyl transferases, e.g., those identified herein including the E. coli ACPS described in the Exemplification section. The term "homolog" of a phosphopantetheinyl transferase is intended to include phosphopantetheinyl transferases from species other than the E. coli ACPS described herein which are capable of phosopantetheinylating the same or different substrates from those of E. coli ACPS. Accordingly, homologs of E. coli ACPS are intended to include any enzyme capable of phosphopantetheinylating a substrate. Phosphopantetheinylation is intended to include the transfer of a phosphopantetheine group from one substrate to another substrate, e.g., the transfer of phosphopantetheine from CoA to an ACP, such as is depicted in FIG. 1. It has been shown, for example, that plant tissues have a phosphopantetheinyl transferase, and it is highly likely that most cells, whether eukaryote or prokaryote also contain at least one enzyme which is capable of phosphopantetheinylating substrates. Homologs of the E. coli ACPS transferase can be isolated using the nucleic acid encoding the E. coli ACPS identified herein. Thus, a nucleic acid encoding a homolog of the E. coli ACPS can be obtained by hybridization of the nucleic acid encoding the E. coli ACPS, or fragment thereof, e.g., a portion encoding motif 1 and motif 2 (as described herein), to libraries of clones containing nucleic acids from specific sources under low or high stringency conditions. Homologs can also be cloned by other methods known in the art, such as by PCR methods using degenerate oligonucleotides having a nucleic acid sequence derived from that of E. coli ACPS. Yet other methods for isolating homologs of the E. coli ACPS include those employing an antibody specific for the E. coli ACPS. Antibodies for use in these methods can be prepared according to methods known in the art.

Accordingly, nucleic acids encoding a phosphopantetheinyl transferase, or fragment thereof, or homolog thereof are also within the scope of the invention.

Homologs of E. coli ACPS, within the scope of the invention can vary in the degree of amino acid sequence homology or identity with the amino acid sequence of E. coli ACPS (Lam et al. (1992) J. Bacteriol. 174:1554; Takiff et al. (1992) J. Bacteriol. 174:1544; SEQ ID NO: 2), so long as the homolog enzyme is capable of phosphopantetheinylating a substrate. Homologs of E. coli ACPS within the scope of the invention can be encoded by a nucleic acid having any degree of nucleic acid sequence homology with a nucleic acid encoding E. coli ACPS (Lam et al. supra; Takiff et al. supra). Homology, also termed herein "identity" refers to sequence similarity between two proteins (peptides) or between two nucleic acid molecules. Homology can be determined by comparing a position in each sequence which may be aligned for purposes of comparison. When a position in the compared sequences is occupied by the same nucleotide base or amino acid, then the molecules are homologous, or identical, at that position. A degree (or percentage) of homology between sequences is a function of the number of matching or homologous positions shared by the sequences. A degree or percentage of "identity" between amino acid sequences refers to amino acid sequence similarity wherein conserved amino acids are considered to be identical for the purpose of determining the degree or percentage of similarity. A conserved amino acid substitution is, e.g., substitution of one amino acid having a negative side chain for another amino acid having a negative side chain.

In a specific embodiment, preferred E. coli ACPS homologs or members of the phosphopantetheine transferase superfamily, have an overall amino acid sequence identity or similarity of at least about 50%, more preferably at least about 60%, more preferably at least about 70%, more preferably at least about 80%, and most preferably at least about 90% with an amino acid sequence shown in SEQ ID NO: 10 or of the phosphopantetheinylating enzymes and/or enzymes having the conserved amino acid motifs described herein. Peptides having an overall amino acid sequence identity or similarity of at least about 93%, more preferably at least about 95%, and most preferably at least about 98–99% with a sequence set forth in SEQ ID NO: 10 or of the phosphopantetheinylating enzymes and/or enzymes having the conserved amino acid motifs described herein are also within the scope of the invention.

Figure 6:
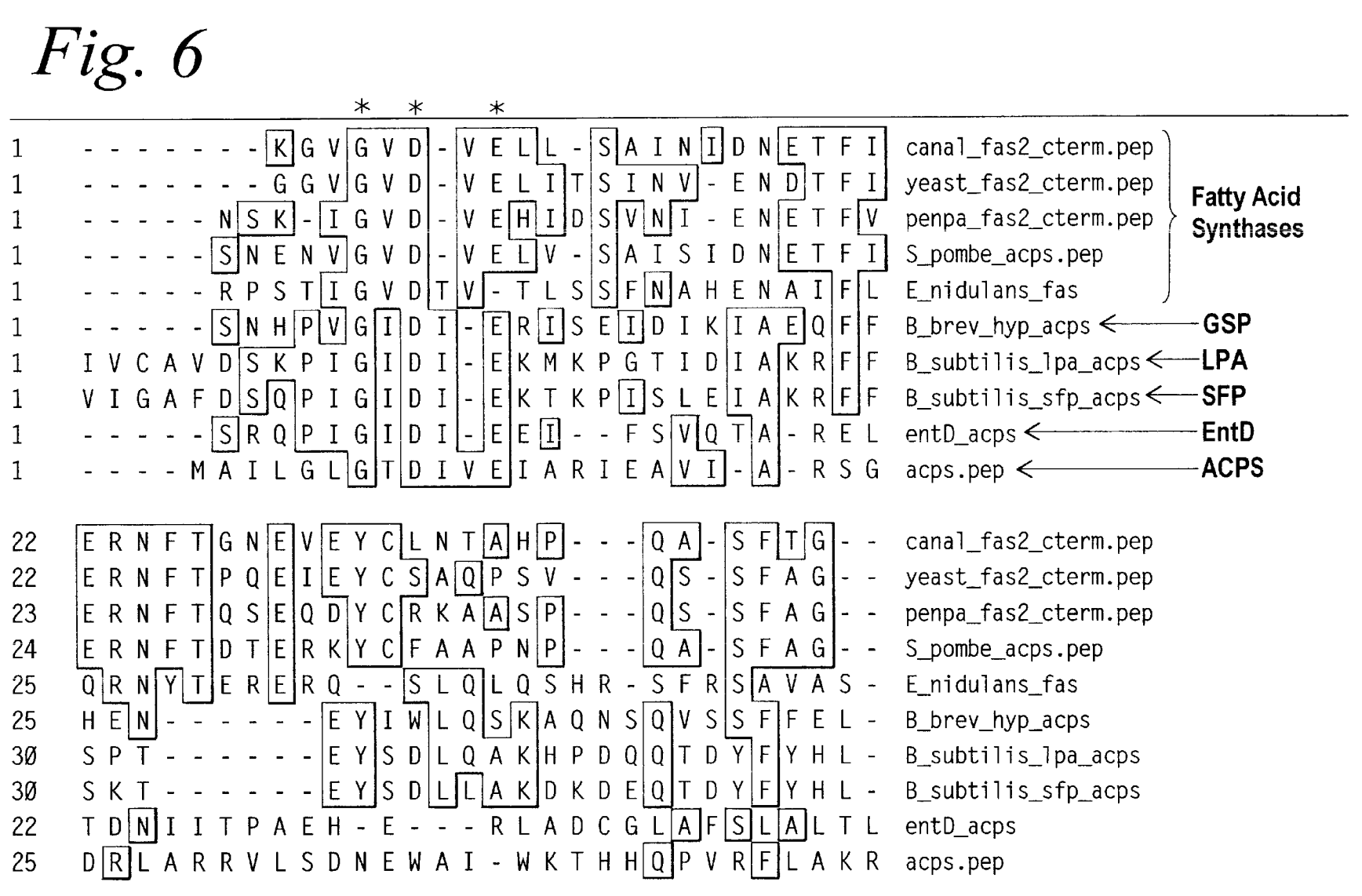
Figure 6:
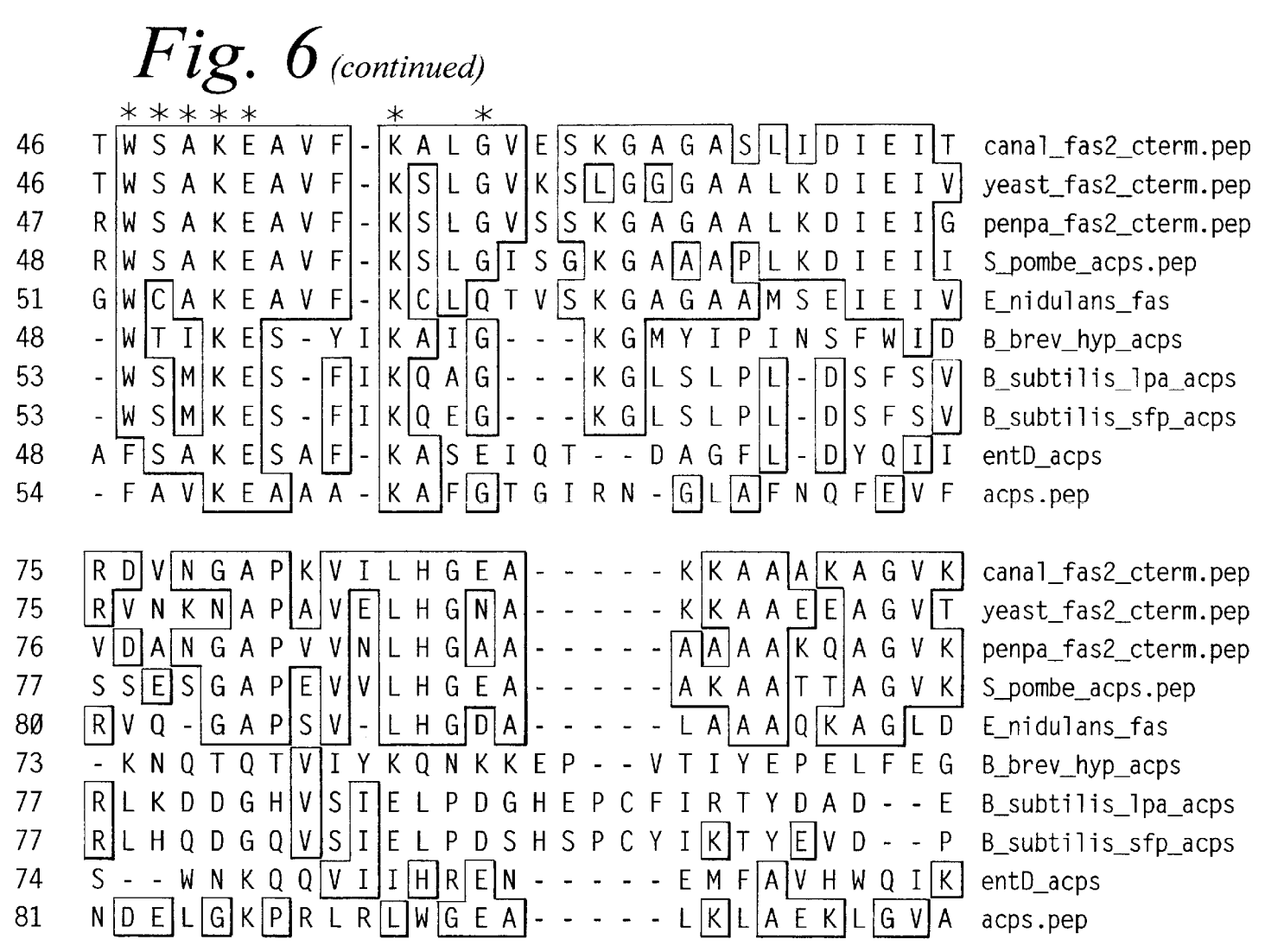
Figure 9:
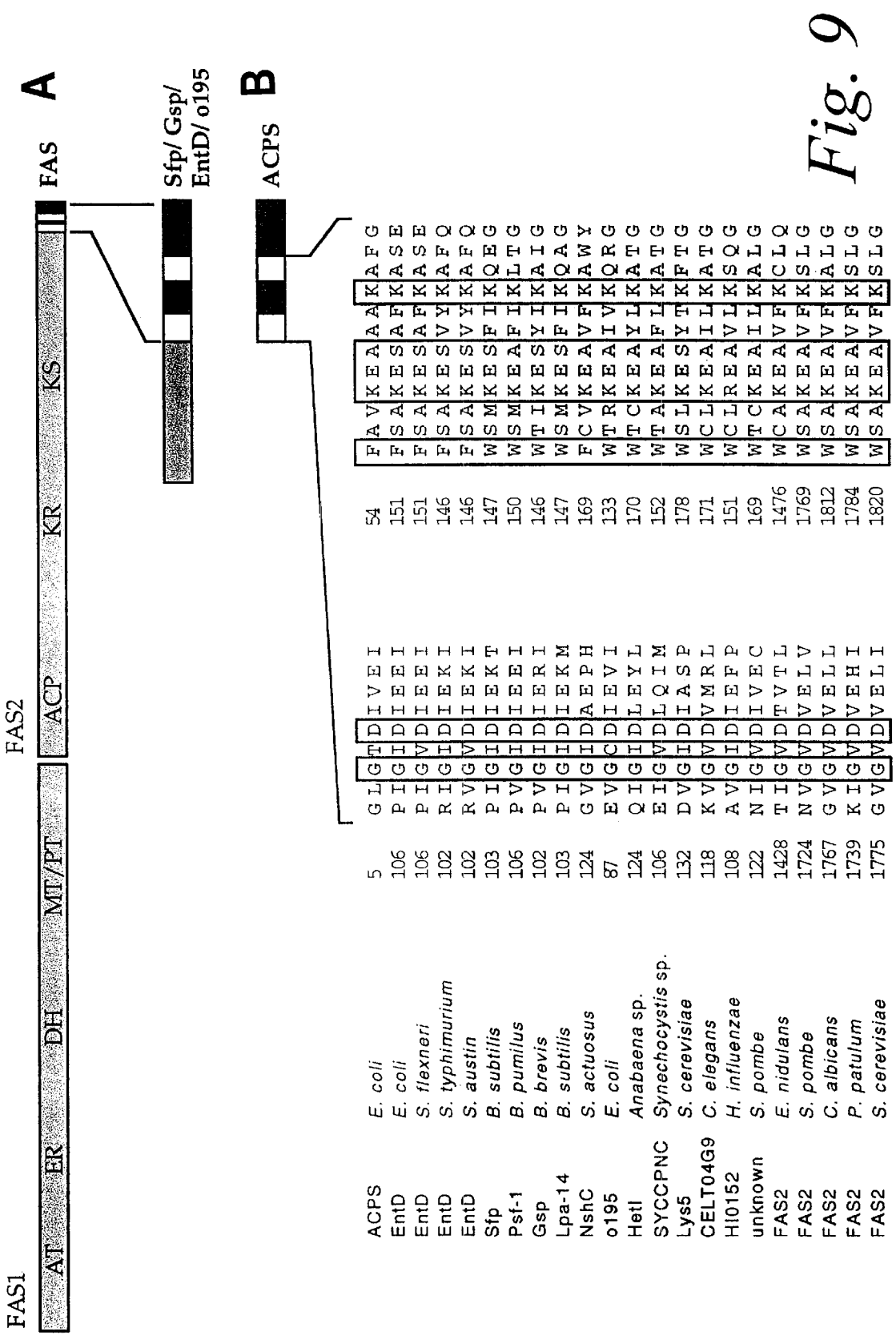
FIG. 9 Panel A is a diagram showing the location of the proposed P-pant transferase domains and the location of consensus sequences (SEQ ID NOS:12–55) in the fungal fatty acid synthases (FAS), the Sfp/Gsp/EntD/o195 homology family, and E. coli ACPS. Component FAS activities are abbreviated as AT, acyl transferase; ER, enoyl reductase; DH, dehydratase; MT/PT malonyl/palmitoyl transferase; ACP, acyl carrier protein; KR, ketoreductase; KS, ketosynthase.

In yet other embodiments of the invention, E. coli ACPS homologs have less than about 50% overall amino acid sequence identity or similarity with an amino acid sequence shown in SEQ ID NO: 10. It has in fact been shown, as described herein, that specific proteins or peptides having limited overall amino acid sequence homology with E. coli ACPS are capable of phosphopantetheinylating substrates. In fact, it has been shown herein, that the B. subtilis protein Sfp, involved in the biosynthesis of surfactin, a cyclic lipopeptide antibiotic, is a phosphopantetheinyl transferase. Another protein, EntD from E. coli, which is involved in the biosynthesis of enterobactin, a secreted iron-scavenging dihydroxylbenzoyl-serine trilactone, is also capable of phosphopantetheinylating substrates. Further, the E. coli protein o195 of unknown function was also shown herein to phosphopantetheinylate substrates. Even though EntD, Sfp, and o195 have only limited overall amino acid sequence homology with E. coli ACPS, the C-terminus of EntD and Sfp have 2 regions of conserved amino acid residues with E. coli ACPS. The regions of homology between the amino acid sequences are represented in FIGS. 6 and 8. Further sequence comparison revealed that these regions of conserved amino acid residues are also present in the following proteins: the Fas2 protein from several organisms, including S. cerevisiae, which is involved in fatty acid synthesis, the Gsp protein from B. brevis which is involved in the synthesis of the peptide antibiotic gramicidin, and the Lpa protein from B. subtilis (FIG. 9). Additional phosphopantetheinyl transferase homologs, listed in FIG. 9, were found to be involved, e.g., in cyanobacterial heterocyst formation and lysine biosynthesis in yeast. Based at least in part on these amino acid sequence homologies, Fas2, Gsp, and Lpa are also likely to be phosphopantetheinyl transferases. Mutagenesis studies have further provided evidence that these conserved regions are required for phosphopantetheinylation of substrates.

Accordingly, preferred phosphopantetheinyl transferases of the invention have at least one or more conserved amino acids, such as the asterisked amino acids shown in FIG. 6 or the regions shown in FIG. 9, or regions of conserved amino acids, such as the boxed amino acid regions in FIGS. 6, 8, and 9. Even more preferred phosphopantetheinyl transferases of the invention have one or more of the following amino acid sequence motifs, wherein X represents any amino acid residue and two amino acids separated by "/" represents a residue which can be either amino acid:

G-X-D-X-X-E (motif 1a) (SEQ ID NO: 57)
G-X-E (motif 1b)
W-S-A K-E-X-X-X-K-X-X (motif 2a) (SEQ ID NO: 58)
F/W-X-X-K/R-E-S/A-X-X-K (motif 2b) (SEQ ID NO: 59)

In an even more preferred embodiment, a phosphopantetheinyl transferase of the invention comprises at least one motif 1 (a or b) and at least one motif 2 (a or b). Yet further preferred phosphopantetheinyl transferases of the invention comprise a motif 1 (a or b) and motif 2 (a or b) separated by at least about 5, preferably at least about 10, more preferably at least about 15, 20, 25, 30, 35, 40, 45, 50, and 55 amino acid residues. In a preferred embodiment, the two motifs are separated by at least about 30 to 45 amino acid residues. Other preferred phosphopantetheinyl transferases of the invention include those comprising amino acid sequences which are significantly homologous or similar to the amino acid sequence of motifs 1a, 1b, 2a, or 2b. Also within the scope of the invention are phosphopantetheinyl transferases which contain a motif 1 and a motif 2 which contain amino acid substitutions, deletions, or additions. Preferred amino acid substitutions are conserved amino acid substitutions, e.g, a substitution of one amino acid for another having a similar characteristic.

Other phosphopantetheinyl transferases within the scope of the invention comprise one or more motifs 1 and 2 having the following amino acid sequences or having one or more conserved amino acid substitutions in these sequences, i.e, substitution of one amino acid with a similar amino acid, or having a deletion of one or more amino acids:

```
motif 1 sequences:

GTDIVEIARI          (SEQ ID NO: 60)

GIDIEEIFSV          (SEQ ID NO: 61)

GIDIEKTKPI          (SEQ ID NO: 62)

GIDIERISEI          (SEQ ID NO: 63)

GVDVELITSI          (SEQ ID NO: 64)

Motif 2 sequences:

FAVKEAAAKAFG        (SEQ ID NO: 65)

FSAKESAFKASE        (SEQ ID NO: 66)

WSMKESFIKQEG        (SEQ ID NO: 67)

WTIKESYIKAIG        (SEQ ID NO: 68)

WSAKEAVFKSLG        (SEQ ID NO: 69)
```

Also within the scope of the invention are phosphopantetheinyl transferases which contain a motif 1 having an amino acid sequence listed above or indicated in the left column of FIG. 9 and a motif 2 having an amino acid sequence listed above or indicated in the right column of FIG. 9. phosphopantetheinyl transferases having amino acid substitutions, e.g., conservative substitutions, deletions or amino acids are also within the scope of the invention. Several assays can be used to confirm that a phosphopantetheinyl transferase having modified or non-modified motif 1 and 2 sequences has a phosphopantetheinylating activity and are described, e.g., in the Examples. Such assays are preferably preformed on various substrates since certain phosphopantetheine transferases show substrate specificity.

Preferred phosphopantetheinylating enzymes have an amino acid sequence identity or similarity of at least about 50%, more preferably at least about 60%, more preferably at least about 70%, more preferably at least about 80%, and most preferably at least about 90% with an amino acid sequence of a motif 1 and a motif 2 shown above or in any Figure. Peptides having an amino acid sequence identity or similarity of at least about 93%, more preferably at least about 95%, and most preferably at least about 98–99% with an amino acid sequence of a motif 1 and a motif 2 shown above or in any Figure are also within the scope of the invention.

Based on the existence of amino acid sequence homologies between phosphopantetheinylating enzymes, it is possible to identify additional phosphopantetheinylating enzymes. Such phosphopantetheinylating enzymes are also within the scope of the invention. Several methods can be used to identify additional phosphopantetheinylating enzymes: amino acid or nucleic acid sequence comparisons and in vitro assays, as described herein.

Figure 5:
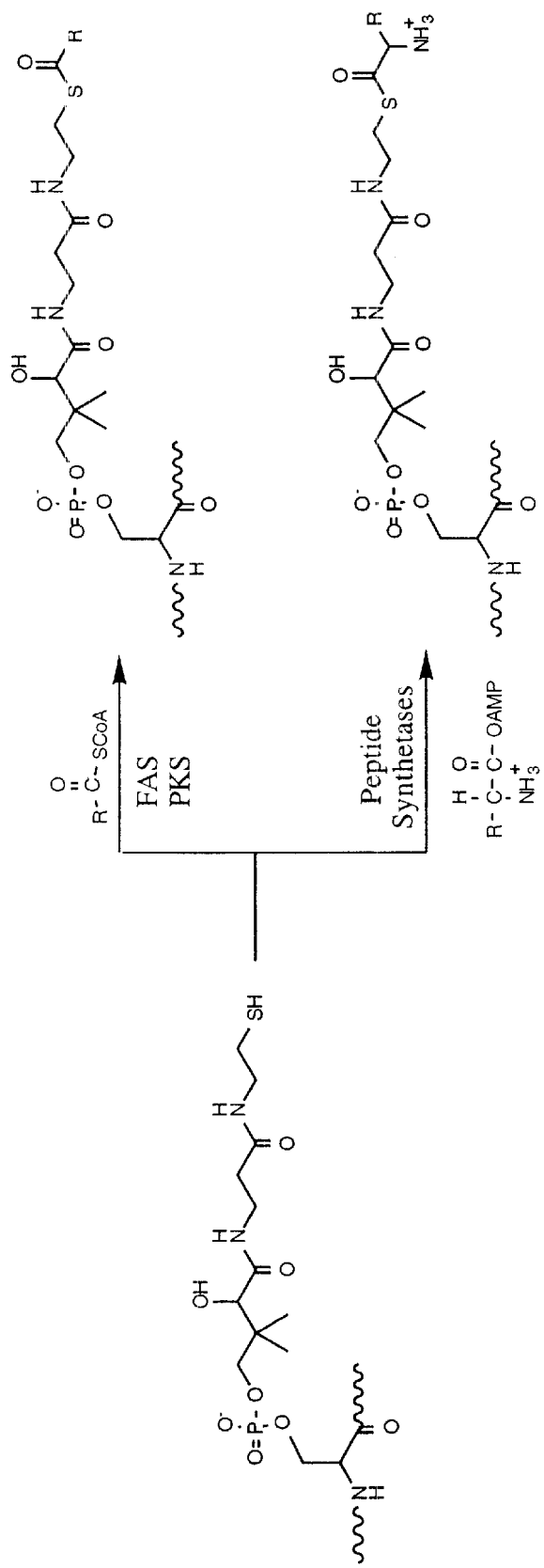
FIG. 5 is a schematic representation of the transfer of an acyl group onto the sulfhydryl group of an ACP by fatty acid synthases (FASs) and polyketide synthases (PKSs) and the transfer of an amino-acyl group onto the sulfhydryl group of an ACP by peptide synthesases.

Enzymes phosphopantetheinlyated according to the methods of the invention may be involved in transfer of various groups onto the newly introduced sulfhydryl (SH) group of the phosphopantetheine prosthetic group which acts as a nucleophile. Acyl-CoAs can be used for fatty acid synthesis (FAS) and all the polyketide synthases (PKS), whereas aminoacyl-AMPs can be used for the peptide synthetases (FIG. 5). In the PKS complexes the acyl-ACPs undergo capture by carbanion nucleophiles for carbon skeleton assembly in polyketide construction while in peptide and depsipeptide synthetases, the aminoacyl-S-ACPs are attacked by nitrogen and oxygen nucleophiles in amide and ester bond forming steps.

A phosphopantetheinyl transferase protein, active fragment thereof, modified phosphopantetheinyl transferase or modified active fragment, and phosphopantetheinyl transferase homologs purified from their natural source or produced as recombinant protein, e.g., according to the techniques described herein can then be used for in vitro phosphopantetheinylation of a substrate, such as an acyl carrier protein. In a specific embodiment, the substrate is a "heterologous" substrate, i.e., a substrate from a species different from the species from which the phosphopantetheinyl transferase originates. It has in fact been shown that a phosphopantetheinyl transferase from one species is capable of phosphopantetheinylating a substrate from another species. For example, several plant enzymes phosphopantetheinylated E. coli ACP as effectively as plant ACP (Elhussein, et al. supra). Furthermore, it has also been shown that E. coli ACPS is capable of phosphopantetheinylating acyl carrier proteins other than E. coli ACP: (1) Lactobacillus D-Alanyl Carrier Protein (DCP) which is active in the biosynthesis of the bacterial cell wall component lipoteichoic acid, (2) Rhizobial NodF which is active in the nodulation process of leguminous vegetables, and (3) Streptomycete ACPs involved in actinorhodin, granaticin, tetracenomycin, frenolicin, oxytetracycline, and tetracenomycin polyketide antibiotic biosynthesis.

In one embodiment, a phosphopantetheinylating enzyme within the scope of the invention is capable of phosphopantetheinylating predominantly a single substrate. In another embodiment of the invention, the phosphopantetheinylating enzyme, e.g. E. coli ACPS, is capable of phosphopantetheinylating a limited number of substrates. In yet another embodiment, the phosphopantetheinylating enzyme has a wide range of substrates.

This invention further provides kits for in vitro phosphopantetheinylation of substrate proteins. Such kits include an isolated or purified phosphopantetheinyl transferase or active fragment thereof as described herein and instructions for use. The phosphopantetheinyl transferase or active fragment thereof can be produced by recombinant technique, chemically synthesized, or purified from a native source. Such phosphopantetheinyl transferase or fragment thereof preferably has a specific activity of at least 250 mU/mg. The phosphopantetheinyl transferase or fragment thereof can be packaged, such that it retains substantially all of the phosphopantetheinylation activity for at least one month, preferably for at least 2 months, even more preferably for at least 3 months. Even more preferably, the phosphopantetheinyl transferase is stable for at least 6 months and most preferably for at least 1 year. For example, the phosphopantetheinyl transferase or fragment thereof can be maintained at −20° C. in a Tris-based buffer containing magnesium and about 20% glycerol. Alternatively, the phosphopantetheinyl transferase or fragment thereof can be provided as a lyophilized powder. The kits can further include a 4'-phosphopantetheinylate group providing reagent, such as Coenzyme A (CoA). In addition, an appropriate reaction buffer for the phosphopantetheinylation reaction, preferably in a concentrated form can be included in the kit. The reaction buffer preferably comprises magnesium ions and Tris buffer.

Compositions comprising a phosphopantetheinyl transferase and an appropriate buffer are also within the scope of the invention. The buffer can be a buffer which maintains or increases the stability of the transferase or which permits the transferase to be maintained in a form under which it maintains its activity or in which its activity can be recovered once the transferase is incubated in appropriate conditions. For example, the buffer can contain an appropriate amount of glycerol, or any other solution allowing the enzyme to be frozen and to be active upon thawing of the transferase. The phosphopantetheinyl transferase can also be in a lyophilized form.

Another embodiment of the invention provides host cells modified to express at least one nucleic acid encoding a phosphopantetheinyl transferase or fragment thereof. Host cells expressing or overexpressing a phosphopantetheinyl transferase have been described herein. In addition, this invention provides host cells transformed with a nucleic acid encoding a non-secreted form of a phosphopantetheinyl transferase or fragment thereof and at least one additional nucleic acid encoding at least one polypeptide. In a preferred embodiment, the at least one polypeptide is a component of the substrate of the phosphopantetheinyl transferase. It is known that expression of heterologous 4'-phosphopantetheine synthases in *E. coli* is limited by the ability of *E. coli* to phosphopantetheinylate large amounts of overproduced protein in vivo. Thus, in one embodiment, the invention provides a method for expressing an active, recombinant form of an enzyme requiring a 4'-phosphopantetheine group by expressing or overexpressing both the enzyme and a phosphopantetheinyl transferase in the same host cell. The enzyme coexpressed in the host cell can be any enzyme which requires phosphopantetheinylation to be active in a reaction. For example, a host cell can be modified to express both the *E. coli* ACPS and the *E. coli* acyl carrier protein or a heterologous substrate, such as NodF or the D-Alanyl Carrier Protein, such that it produces active *E. coli* acyl carrier protein, NodF, or D-Alanyl Carrier Protein, respectively.

In a preferred embodiment of the invention, host cells expressing or overexpressing a phosphopantetheinylating enzyme, e.g., phosphopantetheinyl transferase, or active fragment thereof are used for the production of compounds whose synthesis have at least one step requiring a phosphopantetheinylating enzyme. Such compounds include polyketides (both aromatic and macrolide) and non-ribosomally produced peptides, including depsipeptides, lipopeptides, and glcyopeptides. Biosynthetic pathways that can be modulated with the phosphopantetheinylate transferases of the invention include fatty acids, lipopeptide surfactants and antibiotics. Preferred antibiotics are those non-ribosomally produced peptides, which can be synthesized by a thiotemplate mechanism. Much preferred non-ribosomally produced peptide antibiotics include (a) linear peptides, e.g, Edeine, ACV, Gramacidin, and Alamethicinecyclic peptides, (b) cyclic peptides, e.g., Cyclopeptin, Enterochelin, Ferrichrome, Gramacidin S, Tyrocidine, and Mycobacillin, (c) lactones, e.g., Destruxin, Actinomycin, Etamycin, and Echinomycin, (d) branched cyclopeptides, e.g, Polymyxin and Bacitracin, and (e) Depsipeptides, e.g., Enniatin and Beauvericin (Keinlauf and von Doehren (1990) *Eur. J. Biochem.* 192:1). Other antibiotics within the scope of the invention include erythromycin, clarythromycin, oxytetracycline, bacitracin, cyclosporin, penicillins, cephalosporins, vancomycin. Additional antibiotics within the scope of the invention include those well known in the art, which can be found, e.g., in pharmacology catalogs.

The synthesis of compounds of the invention, e.g, antibiotics can be catalyzed by enzymes including polyketide synthases (which are involved for example in the synthesis of erythromycin and tetracycline), non-ribosomal peptide synthetases, and depsipeptide synthetases. These enzymes belong to the family of acyl carrier proteins, which are homologs of *E. coli* ACP, and require a 4'-phosphopantetheine group for their activity. The ACPs are either type I or type II acyl carrier proteins. The invention thus provides methods for producing compounds, e.g., antibiotics, whose synthesis is catalyzed by either a type I or the type II ACP.

Type I ACPS (also termed type I synthase) are multifunctional enzymes, also termed "multienzyme polypeptides" containing in addition to a domain which is capable of phosphopantetheinylating a substrate, at least some, or all, catalytic activities necessary for peptide formation and activation. Type I ACPS include erythromycin, rapamycin, cyclosporin, avenectin, and tetracycline synthases. Thus, this invention provides a method of producing a compound, e.g., an antibiotic, whose synthesis is catalyzed by a type I ACP, by use of a host cell that has been modified to express a type I ACP and a phosphopantetheinyl transferase to activate the type I ACP. The modified host cell is incubated in a medium containing the necessary substrates for the multienzyme polypeptide. Alternatively, compounds requiring a type I ACP for their synthesis can be produced in vitro with purified enzymes or with recombinantly produced enzymes.

Type II ACPS (also termed type II synthase) are discrete proteins which are capable of associating with several other enzymes to form a multienzyme synthase complex. Type II ACPs are components of tetracyclin, gramicidin, tyrocidin, anthrocyclin, and bacitracin synthetases. Thus, this invention provides a method for producing an antibiotic whose synthesis is catalyzed by a type II ACP by introducing into, and expressing in, a host cell the nucleic acids encoding at least some or all the subunits of the multienzyme complex and a nucleic acid encoding a phosphopantetheinyl transferase and incubating such a modified host cell in a medium containing the appropriate substrates for the enzymes. Alternatively, compounds requiring a type II ACP in their synthesis can be produced in vitro, by contacting purified phosphopantetheinyl transferase(s) and the appropriate enzymes necessary for synthesis of the compound, in an appropriate buffer.

Preferred host cells for producing antibiotics include cells for which the antibiotic is non toxic. Alternatively, a modified form of the antibiotic that is non toxic to the cell can be expressed and the modified form altered in vitro or in vivo to obtain the active form of the antibiotic.

Also within the scope of the invention are organisms which naturally produce antibiotics and which have been modified to express or overexpress a phosphopantetheinyl transferase. Such modified organisms may produce additional quantities of an antibiotic by assuring that the type I or type II ACPs required for their synthesis are in an activated form.

In type I and type II ACPs, the multicomponent system contains a small (e.g., about 80 to 100 amino acids) protein subunit or domain that functions as a carrier protein for the growing acyl chain. These acyl carrier proteins, recognizable by the conserved sequence signature motif D(N,D)FFX(L,I)GG(H,D)S(L,I)X(A,G,C)XX(L,V,M) (SEQ ID NO: 70) (Stein et al. (1995) *Biochemistry* 34:4633) or (L,V)(G,L)(G,A,F,Y)(D,H,K,E)S(L,Q)(D,A,G) (Schlumbohm, W. et al. (1991) *J. Biol. Chem.* 266:23135) (SEQ ID NO:71) are converted from inactive apo forms to functional holo forms by postranslational modification involving attack of the conserved serine $\beta$-$CH_2OH$ side chain on the pyrophosphate linkage of CoA, resulting in transfer of the 4-phosphopantetheine moiety of CoA onto the attacking serine. The newly introduced -SH of the phosphopantetheine (P-pant) prosthetic group now acts as a nucleophile for acylation by a specific substrate, i.e. acyl-CoA and malonyl-CoA derivatives for the fatty acid and polyketide synthases (PKS) and aminoacyl-AMPs for the peptide and depsipeptide synthetases. In the PKS complexes the carboxyactivated malonyl-ACP derivative then undergoes decarboxylation, forming a nucleophilic carbanion species which attacks a second acyl thiolester to yield a new carbon-carbon bond polyketide biosynthesis. In peptide and depsipeptide synthetases, the aminoacyl-ACPs or hydroxyacyl-ACPs serve as nucleophiles in amide and ester bond-forming steps respectively. Thus, phosphopantetheinylation of apo-ACP domains plays a central role in activation of multienzyme synthases responsible for the biogenesis of a vast array of natural products.

Nucleic acids encoding type I and type II ACPs and components associated therewith have been isolated and are described, for example, in the following references: Donadio, S. et al. (1991) *Science* 252:675; Gocht, M. et al. (1994) *J. Bacteriol.* 176:2654; MacCabe, A. et al. (1991) *J. Biol. Chem.* 266:12646; Schweke, T. et al. (1995) *Proc. Natl. Acad. Sci. USA* 92:7839; Ye, J. et al. (1994) *J. Bacteriol.* 176:6270; and Zhang et al. (1995) *J. Bacteriol.* 177: 4009.

In a specific embodiment, the invention provides a phosphopantetheinyl transferase, e.g., an enzyme in which this enzymatic activity is the main function of the enzyme. *E. coli* ACPS is likely to be such an enzyme. In another embodiment, the invention provides phosphopantetheinyl transferase molecules which have additional enzymatic activities, such as a molecule which has both a phosphopantetheinyl transferase and an ACP activity. For example, the yeast fatty acid synthase subunit II (FAS II) has been shown herein to have a domain homologous to *E. coli* ACPS and Sfp, indicating that this enzyme could act intramolecularly to add a phosphopantetheinyl unit to Ser-180, the putative ACP domain of this polyprotein. Accordingly, the invention provides polyfunctional or polyenzymatic proteins comprising as one of the various enzymatic functions, the ability to transfer phosphopantetheinyl groups. Such transfer can be onto the same or another molecule.

The invention further provides proteins which do not normally possess the ability to phosphopantetheinylate, but which may be modified to obtain this enzymatic activity. For example, a peptide capable of transferring a phosphopantetheinyl group can be grafted onto, or linked to, another protein by, e.g., chemical cross-linking or recombinant methods. In a preferred embodiment, at least one phosphopantetheinyl transferase or active fragment thereof is linked to a protein which is an ACP. The transferase activity that is grafted can be from *E. coli* ACPS, from Sfp, or any other protein having such catalytic activity.

Other compounds whose synthesis require a type I and type II ACP (also termed type I and type II synthases, respectively) and which thus require phosphopantetheinylation by a phosphopantetheinyl transferase include immunosuppressant agents (e.g., FK506 antifngal agents (e.g., amphotericin), antiparasitic agents, cardiovascular agents (e.g., lovastatin) and antitumor agents (e.g., anthracyline) agents among others. Thus, also within the scope of the invention are methods for producing such compounds using the phosphopantetheinyl transferases, active fragments thereof and expression systems described herein.

Methods for producing purified phosphopantetheinyl transferase are also within the scope of the invention. In one embodiment, a phosphopantetheinyl transferase or active fragment thereof is isolated from a cell naturally producing the enzyme, such as *E. coli* and purified by a factor of at least about 1,000 fold, more preferably at least about 10,000 fold and even more preferably at least about 50,000 fold. Methods for isolating the enzyme preferably include an affinity purification step over a column containing apo-acyl carrier protein. Such methods are further described in detail herein. The purified phosphopantetheinyl transferase preferably has a specific activity of 250 mU/mg of protein, more preferably 400 mU/mg, and even more preferably 500 mU/mg of protein. The invention also provides methods for producing recombinant forms of phosphopantetheinyl transferases. Such methods comprise transforming a host cell with a nucleic acid encoding a phosphopantetheinyl transferase, under conditions appropriate for expression of the protein and isolating the synthase from the host cells and culture media. A purified recombinant phosphopantetheinyl transferase preferably has a specific activity of 200 mU/mg, and more preferably 250 mU/mg.

Also within the scope of the invention are methods for identifying inhibitors of a phosphopantetheinyl transferase. An inhibitory compound is defined as a compound that reduces or inhibits phosphopantetheinylation of a substrate by a phosphopantetheinyl transferase. Inhibitors of phosphopantetheinyl transferase can be identified by using an in vitro or an in vivo test. In one embodiment, potential inhibitory compounds are screened in an in vitro phosphopantetheinylation assay, such as an assay described in the Exemplification section. In another embodiment, potential inhibitory compounds are contacted with a microorganism having a phosphopantetheinyl transferase and the phosphopantetheinylation of substrate is monitored. Inhibitory compounds can be used, for example, for blocking specific pathways requiring phosphopantetheinylation in microorganisms, such as ACP dependent pathways. ACPs are involved, for example, in the transacylation of proteins, such as haemolysin, a pathogenic factor of *E. coli*. The identification of the yeast protein Lys 2, involved in a primary lysine biosynthetic pathway, as a phosphopantetheinylating enzyme, provides a method for killing yeast.

Accordingly, inhibitors of phosphopantetheinylating enzymes can be used as anti-fungal agents. Moreover, many membrane-associated proteins are acylated and blocking or reducing acylation of these proteins in a microorganism can potentially affect the viability of the microorganism. ACPs have also been involved in transacylation of cell wall components, which are popular therapeutic targets. Other reactions involving ACPs include transacylation of oligosaccharides, involved for example in the nodulation factors of Rhizobia genus. Transacylation of oligosaccharides are an essential step in nodule formation in nitrogen fixing plants and has agricultural applications.

Yet other embodiments within the scope of the invention include screening methods to uncover novel antibiotics. In one embodiment of the invention, novel antibiotics are identified by coexpressing in a host cell a library of various forms of type I or type II ACPs, such as modified ACPs obtained by random mutagenesis and/or a phosphopantetheinyl transferase, or mutated form thereof, which is required for phosphopantetheinylation and thus activation of the ACPs. Similarly, the invention provides methods for isolating novel immunosuppressant, antifungal, antihelminthic, antiparasitic, and antitumor agents.

It has been shown herein that the *E. coli* EntD gene which encodes a product necessary for the synthesis of the iron-chelating and transport molecule enterobactin (Ent) shows significant amino acid sequence homology with the phosphopantetheinyl transferases *E. coli* ACPS and Sfp, and that it phosphopantetheinylates at least two substrates, ACP and PCP. Accordingly, the invention provides methods for modulating iron uptake by bacteria. In one embodiment, the invention provides a method for improving iron uptake of bacteria, such as by expressing in bacteria the gene EntD. Improved iron uptake can result in more efficient bacterial growth, which will be useful in cases where bacteria are grown for the production of a beneficial compound. The invention also provides methods for reducing iron uptake by bacteria, such as by growing bacteria in the presence of an inhibitor of phosphopantetheinylation. Such an inhibitor can be isolated as described above and in the exemplification section. Accordingly, the invention provides a method for inhibiting bacterial growth or killing of bacteria by iron deprivation.

The invention will also be useful for the design of strategies for heterologous production of functional polyketide and polypeptide synthetases, e.g., in combinatorial biosynthesis of "unnatural" natural products. For example, new drug molecules can be made by genetically altering gene clusters in an organism, such as Streptomyces, that synthesize polyketides. Then the modified genes, e.g., produced in *E. coli* can be reinserted in the Streptomyces where new polyketides are expressed. Such a process can be applied to the synthesis of a variety of compounds in addition to polyketide antibiotics. Thus, processes for producing new compounds in a host or in vitro, by using modified, e.g., mutated phosphopantetheinylating enzymes, are within the scope of the invention. Preferred biosynthetic pathways that can be modified according to this method include those in involved in the biosynthesis of erythromycin, the anticancer drug daunorubicin, and the immunosuppressant, rapamycin.

This invention is further illustrated by the following examples which should not be construed as limiting. The contents of all references, patents, and published patent applications cited throughout this application are hereby incorporated by reference.

EXAMPLE 1

Cloning and Overproduction of the *Escherichia coli* Holo-Acyl Carrier Protein Synthase Materials and Methods Preparation of [$^3$H]Coenzyme A. CoA (220 mg) was labeled by tritium gas exposure (New England Nuclear) to yield 600 mCi of crude material. This material was added to unlabeled CoA and the mixture was acylated and purified as described by Elovson and Vagelos (supra). In this manner, [$^3$H]CoA with specific activities as high as $7 \times 10^{14}$ dpm/mol and having 70% of the $^3$H-label in the phosphopantetheine portion was prepared.

Assay of phosphopantetheinyl transferase Activity. In a typical assay, 100 μM [$^3$H]CoA, 50 μM apo-ACP, 10 mM $MgCl_2$, 50 mM Tris.HCl, pH 8.8, and ACPS in a final volume of 100 μL were incubated at 37° C. for 30 min in a 1.5 mL microcentrifuge tube. Reactions were quenched with 800 μL 10% TCA. BSA (20 μL of a 25 mg/mL solution) was then added to facilitate precipitation of radiolabeled protein. The 1.5 mL tubes were centrifuged at 12,000×g for 5 min. Supernatants were removed and the pellets were rinsed with 3×900 μL of 10% TCA. Residual TCA was collected by centrifugation, and the pellets were resuspended in 150 μL of 1 M Tris base. The resuspended pellets were transferred to scintillation vials, 2.5 mL of scintillation cocktail (Packard) was added and the amount of $^3$H-labeled holo-ACP formed was quantified by liquid scintillation counting.

Confirmation of in vitro Holo-ACP Formation by native-PAGE, Autoradiography and Mass Spectrometry. ACPS assays were incubated for 12 h at 37° C. Control assays were worked up in the usual manner, and holo-ACP formation was confirmed by liquid scintillation counting. Assay mixtures for native-PAGE were not quenched with 10% TCA. The ACPS assay mixture was divided into two equal portions. To one 50 μL portion was added 20 μL of 5× native-PAGE sample buffer (Ausubel, F. M., et al. (1992) *Short Protocals in Molecular Biology*, John Wiley & Sons, New York) which contained DTT whereas the other sample was not reduced with DTT. These samples were analyzed by 20% native gel electrophoresis followed by Coomassie staining. The stained gels were soaked in Amplify (Amersham) for 15 min before drying under vacuum. The dried gels were autoradiographed at −80° C. followed by photographic development (FIG. 2). Holo-ACP-SH migrates slightly faster than apo-ACP on 20% native gels whereas holo-ACP dimer migrates considerably slower (Rock, C. O. and Cronan, J. E., Jr. (1981) *Methods Enzymol.* 71:341–351).

Overproduction and Purification of Apo-ACP. *E. coli* DK554, an apo-ACP overproducer strain, was provided by Prof. John E. Cronan, Jr. (Department of Microbiology and Biochemistry, University of Illinois at Urbana-Champaign). Cultures grown in Terrific Broth supplemented with 50 mM glucose, 25 μM pantothenate and 50 μg/mL kanamycin were induced with 1 mM IPTG at an O.D. of 0.8. Cells were lysed by two passages through a French pressure cell at 10,000 psi. The majority of overproduced ACP was present in the apo-form. Minor amounts of holo-ACP were converted to apo-ACP using endogenous holo-ACP hydrolase by incubating the lysate with 10 mM $MgCl_2$ and 2 mM $MnCl_2$ for 60 min at 25° C. with stirring (Fischl, A. S. and Kennedy, E. P. (1990) *J. Bacteriol.* 172:5445–5449). Apo-ACP was then purified following the procedure of Rock and Cronan (supra) to yield 60 mg per L culture.

Purification of ACPS from *E. coli* K-12. A 500 g frozen block of *E. coli* K-12 cells (ATCC 14948) grown to ¾ log phase (University of Alabama Fermentation Facility) was broken into smaller pieces with a mallet and added to 1 L of 50 mM Tris, 10 mM MgCl$_2$, 1 mM DTT, 1 mM PMSF, 1 mM benzamidine, 50 μM CoA, and 5% (w/v) glycerol, titrated to pH 8.1 with 1 M MES. The cells were lysed by a single passage through an Amicon French pressure cell at 8,000–16,000 psi. Cellular debris was removed by centrifugation at 8,000×g for 30 min to yield 1.5 L of crude extract. The supernatant was added to 150 g of DE-52 slurry (Whatman) in 50 mM Tris.HCl, pH 8.0 and mixed gently for 15 min at 4° C. DE-52 was removed by centrifugation and the supernatant was treated once again with 150 g of DE-52, pH 8.0. After the removal of the DE-52 resin the supernatant was clarified further by centrifugation at 16,000×g for 30 min.

Figure 3:
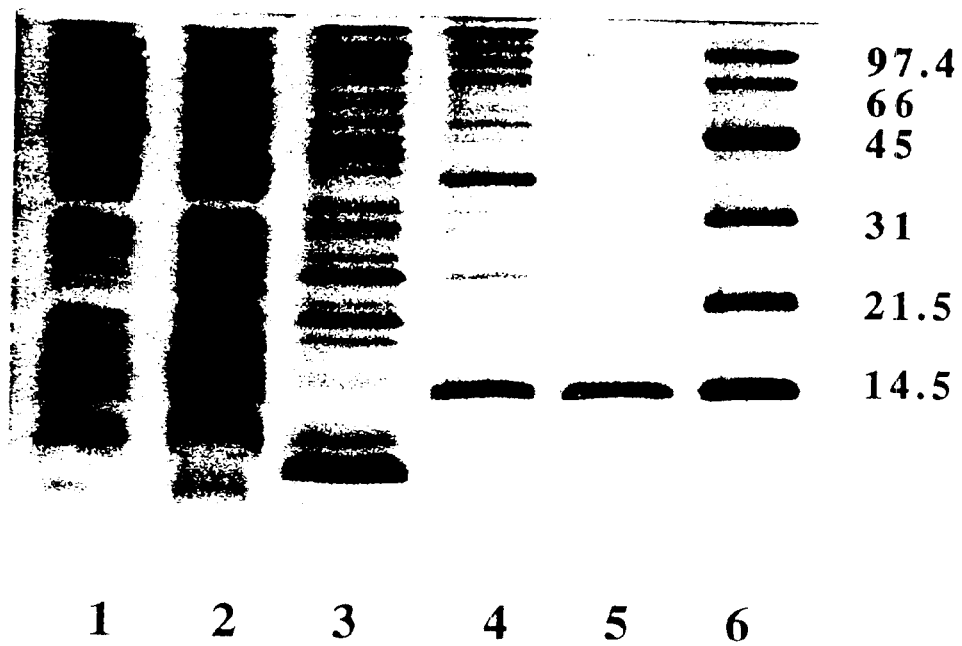
FIG. 3 shows the results of Tris-Tricine SDS-PAGE analysis of fractions from purification of wild-type and recombinant ACPS (lane 1, crude lysate of *E. coli* K-12; lane 2, DE-52 supernatant; lane 3, SP-Sepharose pool; lane 4, apo-ACP affinity column pool (0.5 mL sample concentrated 20-fold by acetone precipitation); lane 5, SP-Sepharose purified recombinant ACPS).

The clarified extract (1.3 L) was titrated to pH 6.5 with a saturated MES solution and was then loaded at a flow rate of 10 mL/min onto a 3×30 cm SP-Sepharose column (Pharmacia) which had been pre-equilibrated with 50 mM MES, 10 mM MgCl$_2$, 5% (w/v) glycerol, pH 6.1 (Buffer A). After the extract was loaded, the column was washed with 750 mL of Buffer A while collecting 25 mL fractions. The column was then eluted with a linear 0 to 1 M NaCl gradient (1 L) in Buffer A. Active fractions were pooled to yield 190 mL. This 190 mL SP-Sepharose purified material was next loaded at a flow rate of 2 mL/min onto a 2.5×4.0 cm Affi-Gel 15 apo-ACP affinity column (BioRad, Hercules, Calif., prepared following the manufacturer's instructions) while collecting 25 mL fractions. The column was washed with 100 mL of Buffer A, and ACPS was then eluted with 50 mL of 6 M guanidinium.HCl in 50 mM MES, pH 6.1 while collecting 8 mL fractions. phosphopantetheinyl transferase activity was reconstituted by diluting the guanidinium.HCl to a final concentration <2M in the assay mixture. Active fractions were pooled to yield 16 mL which was then dialyzed against 2×1 L of Buffer A to yield about 0.2 mg protein of apparent 70,000-fold purity (Table 1). Tris-Tricine SDS-PAGE analysis (Schagger, H. and von Jagow, G. (1987) *Annal. Biochem.* 166:368–379) revealed the presence of only a few major bands (FIG. 3). Previous purifications had demonstrated that the 14 kDa band copurified with the phosphopantetheinyl transferase activity (data not shown). Aliquots (500 μL) of the affinity purified protein were concentrated by acetone precipitation. The precipitated protein was resolved by 16% T, 6% C Tris.Tricine SDS-PAGE and then electroblotted to a Pro-Blot membrane (Applied Biosystems Inc., Foster City, Calif.) following the manufacturer's instructions. Proteins were visualized by staining briefly with 0.1% amido black in 1% acetic acid. The 14 kDa protein was excised and submitted for N-terminal sequencing.

TABLE 1

Purification of wild-type ACPS from *E. coli* K-12

| fraction | protein mg | activity mU[a] | specific activity mU · mg$^{-1}$ | -fold | % Overall Yld. |
|---|---|---|---|---|---|
| Crude extract | 50,000 | 420 | 8.4 10$^{-3}$ | — | — |
| DE-52 | 13,000 | 340 | 2.6 × 10$^{-2}$ | 3 | 80 |
| SP-Sepharose | 260 | 320 | 1.2 | 140 | 75 |
| Apo-ACP affinity | ~0.2 | 120 | ~600 | ~70,000 | 30 |

[a]One unit of activity produces 1 μmol holo-ACP per minute.

Cloning and Overexpression of the dpj gene. The dpj gene was amplified using a freshly-grown single colony of *E. coli* strain BW13711 as template in the polymerase chain reaction (PCR). *E. coli* strain BW13711, a gift from Professor Barry Wanner of Purdue University, has a lacX74 deletion of the entire lac operon but is otherwise wild-type *E. coli* K-12 that has been cured of lambda and the F factor. The forward primer incorporated an NdeI restriction site at the start codon:
5'-TGTACCTCAGACCATATGGCAATATTAGGTTT AGGCACGG-3' (SEQ ID NO: 72). The reverse primer incorporated a HindIII restriction site after the stop codon:
5'-TGATGTCAGTCAAGCTTAACTTTCAATAATTAC CGTGGCA-3' (SEQ ID NO: 73). The resulting PCR product was subcloned into the NdeI/HindIII site of the pET22b expression plasmid (Novagen) using standard molecular biology procedures and designated pDPJ (Asubel, F. M., et al. supra). *E. coli* BL21(DE3) was transformed with supercoiled pDPJ.

Three 1 L cultures of *E. coli* BL21 (DE3)pDPJ in 2×YT media supplemented with 50 μg/mL ampicillin were grown at 37° C., 250 rpm to an O.D. of 0.8–1.0 before transferring the cultures to 30° C., 250 rpm and inducing with 100 μM IPTG. Cultures were grown at 30° C. for an additional 3 h and were then harvested by centrifugation. Cells were resuspended (5 mL/g wet cell mass) in 50 mM Tris.HCl, 10 mM MgCl$_2$, 5% glycerol, pH 8.0 (Buffer B) and lysed by two passages through a French pressure cell at 10,000–15,000 psi. Cellular debris was removed by, centrifugation at 16,000×g for 30 min. The cell free extract was then treated twice with an equal volume of DE-52 slurry (pH 8.0). The DE-52 supernatant was adjusted to pH 6.5 with a saturated MES solution and loaded onto a 3×30 cm SP-Sepharose column which had been pre-equilibrated with Buffer A. The column was washed with 250 mL Buffer A. ACPS was then eluted with a linear 500 mL, 0 to 1 M NaCl gradient.

Results

In order to initiate purification of ACPS, a rapid and reliable assay for monitoring phosphopantetheinyl transferase activity through the purification process was sought. Of the several methods described for the in vitro determination of phosphopantetheinyl transferase activity (Elovson, J. and Vagelos, P. R. supra; Elhussein et al. supra; Polacco, M. L. and Cronan, J. E., Jr. supra) the direct-discontinuous radioassay employing [$^3$H]-(pantetheinyl)-CoA and apo-ACP was chosen. The amount of phosphopantetheinyl transferase activity is measured by monitoring the rate at which radiolabeled pantetheine gets incorporated into holo-ACP. Radiolabeled holo-ACP is quantified by co-precipitation with BSA using 10% TCA followed by liquid scintillation counting of the protein pellet. The formation of 3H-labeled holo-ACP was confirmed by autoradiography of 20% native polyacrylamide gels.

Earlier reports had indicated that ACPS is a basic protein which would not bind to anion exchange resins (Elovson, J. and Veglas, P. R. supra). A 3-fold purification was thereby quickly achieved by batchwise DE-52 treatment. The DE-52 supernatant was then adsorbed onto the cation exchanger resin SP-Sepharose. Following an extensive wash, the column was eluted using a linear NaCl gradient (0–1 M). ACPS activity eluted at approximately 0.35 M NaCl. The submicromolar $K_m$ of ACPS for apo-ACP previously measured with 780-fold purified enzyme (Elovson, J. and Veglas, P. R. supra) suggested a very tight binding interaction suitable for affinity chromatography. Apo-ACP was linked to an Affi-Gel 15 matrix and it was found that phosphopantetheinyl transferase activity was indeed tightly retained by the apo-ACP affinity column. Phosphopantetheinyl transferase activity did not elute with either high salt or low pH, although it did elute with apo-ACP. Unfortunately, apo-ACP elution was not suitable for subsequent purification steps since separation of the apo-ACP from ACPS was difficult and trace contaminants in the apo-ACP preparation prevented identification of the low abundance ACPS protein. The elution requirement was satisfied when it was shown that the ACPS could be refolded and its activity reconstituted following elution with chaotropes under denaturing conditions by subsequent dilution of the denaturant. While both urea and guanidinium.HCl proved suitable for this purpose, guanidinium.HCl (6M) was chosen as the preferred eluant to minimize the risk of N-terminal carbamylation of the target protein. Guanidinium.HCl elution of ACPS activity from the apo-ACP affinity column yielded an apparent 70,000-fold purified preparation. Tris-Tricine SDS-PAGE analysis (Schagger, H. and von Jagow, G. supra) revealed the presence of only a few major bands (FIG. 3). Previous purifications had demonstrated that the 14 kDa band copurified with the ACPS activity (data not shown). Using the standard Tris.glycine SDS-PAGE analysis the 14 kDa protein migrated with the buffer front, greatly hampering initial detection of a candidate band for N-terminal sequence analysis. Tris.Tricine SDS-PAGE analysis offers greater resolution of low molecular weight proteins and was therefore used for all subsequent analyses of ACPS containing fractions. Superdex-75 gel filtration chromatography of the ACPS preparation indicated a native molecular weight of approximately 30,000, suggesting that the native enzyme is a homodimer (data not shown). The 14 kDa protein was electroblotted and submitted for N-terminal sequencing. Twenty-five cycles of N-terminal sequencing yielded a primary sequence of AILGLGTDIVEIARIEAVIARSGDR (SEQ ID NO: 74). A BLAST search (Altschul, S. F., et al. (1990) *J. Mol. Biol.* 215:403–410) of the non-redundant protein database revealed that the 14 kDa protein is encoded by dpj (downstream of Pyridoxal J), the second gene in the pdxJ operon (Takiff, H. E., et al. (1992) *J. Bacteriol.* 174:1544–1553).

The dpj gene was amplified from the *E. coli* genome by PCR and subcloned into the NdeI/HindIII restriction site of the pET22b vector (Novagen). Induction of *E. coli* BL21 (DE3)pDPJ and purification of the phosphopantetheinyl transferase activity yielded 50 mg of protein with >95% purity and 320 mU/mg specific activity (Table 2). This corresponds to at least one-half the specific activity of the partially pure wild-type preparation. This difference is most probably due to errors associated with quantification of the dilute wild-type protein preparation using the Bradford protein assay. DNA sequencing of the pDPJ construct confirmed the recombinant sequence was correct (Dana-Farber Molecular Biology Core Facility, Boston, Mass.). The 14 kDa overproduced recombinant protein was blotted and submitted for N-terminal sequencing which confirmed the first ten residues as the dpj gene product. Mass spectrometric analysis indicated a molar mass of 13,950 within 0.2% of the calculated mass of 13,922. Incorporation of the [$^3$H] phosphopantetheine moiety into apo-ACP by recombinant enzyme was again confirmed by 20% native gel electrophoresis followed by autoradiography (FIG. 2). Holo-ACP migrates slightly faster than apo-ACP on 20% native-PAGE (14). Furthermore, mass spectral analysis of unlabeled enzymatic holo-ACP product indicated a MW of 8841 (calculated 8847) in contrast to an observed MW of 8518 (calculated 8508) for the apo-ACP substrate. Steady-state kinetics on recombinant ACPS using the [$^3$H]CoA radioassay yielded a $K_m$ value of 50 $\mu$M for CoA. As previously reported with partially purified ACPS (Elovson & Vagelos (1968), supra), we observed substrate inhibition at apo-ACP concentrations greater than 2 $\mu$M. However, we were able to assign an upper limit of ~1 $\mu$M to the $K_m$ value for apo-ACP.

An apparent $k_{cat}$ value of about 10 min$^{-1}$ was measured at saturating CoA and 50 $\mu$M apo-ACP. Identical $K_m$ values were obtained for apo-ACP and CoA with wild-type ACPS under the same assay conditions. Differences between our kinetic constants and those reported previously, 0.4 $\mu$M and 150 $\mu$M for $K_m$(apo-ACP) and $K_m$(CoA) respectively (Elovson, J. and Vagelos, P. R. supra), are most likely attributable to variations in the apo-ACP and CoA substrate preparations and the assay conditions employed.

TABLE 2

Purification of recombinant ACPS from *E. coli* BL21(DE3)pDPJ

| fraction | protein mg | activity U$^a$ | specific activity mU · mg$^{-1}$ | -fold | % Overall Yld. |
|---|---|---|---|---|---|
| Crude extract | 600 | 120 | 200 | — | — |
| DE-52 | 160 | 40 | 250 | 1.3 | 27 |
| SP-Sepharose | 50 | 16 | 320 | 1.6 | 13 |

$^a$One unit of activity produces 1 $\mu$mol holo-ACP per minute.

In vitro Phosphopantetheinylation of NodF with Recombinant *E. coli* ACPS.

This example shows that *E. coli* ACPS phosphopantetheinylates the heterologous substrate Rhizobial NodF.

The conditions of the in vitro phosphopantetheinylation assay used in this example are the same as those described above using the *E. coli* ACP as a substrate. The efficiency of phosphopantetheinylation of wild-type NodF, an ACP-NodF chimera, and wild-type ACP by *E. coli* ACPS are presented below:

| NodF | 5 $\mu$L of 1.9 mg/mL stock per assay | |
|---|---|---|
| +ACPS | 236 000 dpm | 47% conversion |
| −ACPS | 15 500 dpm | |
| ACP::NodF | 5 $\mu$L of 1.2 mg/mL stock per assay | |
| +ACPS | 122 000 dpm | % conversion |
| −ACPS | 15 900 | |
| ACP | 5 $\mu$L of 8.5 mg/mL stock per assay | |
| +ACPS | 1 320 000 dpm | 46% conversion |
| −ACPS | 22 900 | |

The values are averages of 3 replicate assays. The associated errors were 5%, 20%, and 10% for the ACP, ACP::NodF, and NodF assays, respectively. The % conversion was calculated using the specific activity for the pantetheine moiety of the radiolabeled CoA, which is 4.8×10$^8$ dpm/umol.

In vitro Phosphopantetheinylation of D-Alanyl Carrier Protein with Recombinant *E. coli* ACPS This example shows that *E. coli* ACPS is capable to phosphopantetheinylate in vitro D-Alanyl carrier protein (Dcp), such as *Lactobacillus casei* Dcp.

The conditions of the in vitro phosphopantetheinylation reaction were essentially the same as those described in the previous examples except for the 36 hour incubation time and an increase in the initial CoA concentration. Again, all assays were run in triplicate at 37° C. The reactions were quenched with 800 $\mu$L, 10% TCA and 500 $\mu$g BSA was added. The 1.5 mL eppendorf tubes were mixed thoroughly by inversion and the protein was pelleted by centrifugation at 12,000×g. The pellets were washed.3× with 900 $\mu$L 10% TCA and then resolubolized in 150 $\mu$L 1 M Tris base. The resolubolized protein was then added to 3 mL Packard liquid scintillation cocktail and the amount of radioactivity incorporated into the protein fraction was quantified.

Dcp:ACPS Assays (3× with ACPS, 3× without ACPS)

| per 100 μL assay | final concentration |
|---|---|
| 5 μL apo-Dcp, 0.8 nmol/μL | 40 μM |
| 5 μL 0.2M MgCl$_2$ | 10 mM |
| 5 μL 50 mM DTT | 2.5 mM |
| 5 μL 1.5M Tris-HCl, pH 8.5 | 75 mM |
| 30 μL [$^3$H]CoA, 0.7 mM | 210 μM |
| ~7.0 × 10$^{14}$ dpm/mole overall | |
| ~4.9 × 10$^{14}$ dpm/mole w.r.t. pantetheine | |

40 μL H$_2$O

10 μL 18 μM ACPS, 1.5 mUnits 1.8 μM

ACP:ACPS Assays (3× with ACPS, 3× without ACPS)

| per 100 μL assay | final concentration |
|---|---|
| 5 μL apo-ACP, 1 mM | 50 μM |
| 5 μL 0.2M MgCl$_2$ | 10 mM |
| 5 μL 50 mM DTT | 2.5 mM |
| 5 μL 1.5M Tris-HCl, pH 8.5 | 75 mM |
| 30 μL [$^3$H]CoA, 0.7 mM | 210 μM |
| ~7.0 × 10$^{14}$ dpm/mole overall | |
| ~4.9 × 10$^{14}$ dpm/mole w.r.t. pantetheine | |
| 50 μL H$_2$O | |
| 10 μL 18 μM ACPS, 1.5 mUnits | 1.8 μM |

The results are presented in Table III:

TABLE III

| | |
|---|---|
| Dcp + ACPS | 1.04 × 10$^6$(±0.93%) |
| " | 1.00 × 10$^6$(±0.77%) |
| " | 0.98 × 10$^6$(±0.95%) |
| Dcp − ACPS | 6.91 × 10$^4$(±1.92%) |
| " | 6.75 × 10$^4$(±1.95%) |
| " | 6.69 × 10$^4$(±1.95%) |
| ACP + ACPS | 2.13 × 10$^6$(±.65%) |
| " | 2.20 × 10$^6$(±.64%) |
| " | 2.21 × 10$^6$(±.63%) |
| ACP − ACPS | 3.40 × 10$^4$(±1.94%) |
| " | 3.75 × 10$^4$(±1.99%) |
| " | 3.60 × 10$^4$(±1.96%) |

Thus, these results indicate that *E. coli* ACPS is capable of phosphopantetheinylating Dcp.

In another example, varying concentrations of apo-Dcp were incubated with ACPS at 37° C. to determine extent of phosphopantetheinylation.

Final Destinations. stock solids

| | | | |
|---|---|---|---|
| 1.8 μM | Recombinant ACPS | 10 μL | 18 μM |
| | vary apo-Dcp | 5 μL | 10, 20, 50, 100, 200, 300, 400, 500 μM |

-continued

| | | | |
|---|---|---|---|
| 210 μM | [$^3$H]CoA | 30 | 0.7 mM |
| 10 mM | MgCl$_2$ | 5 | 0.2 mM |
| 23 mM | DTT | 5 | 50 mM |
| 75 mM | Tris HCl pH 8.0 | 5 | 1.5M |
| | H$_2$O | 40 | |

The assays were incubated overnight at 37° C.

Figure 4:
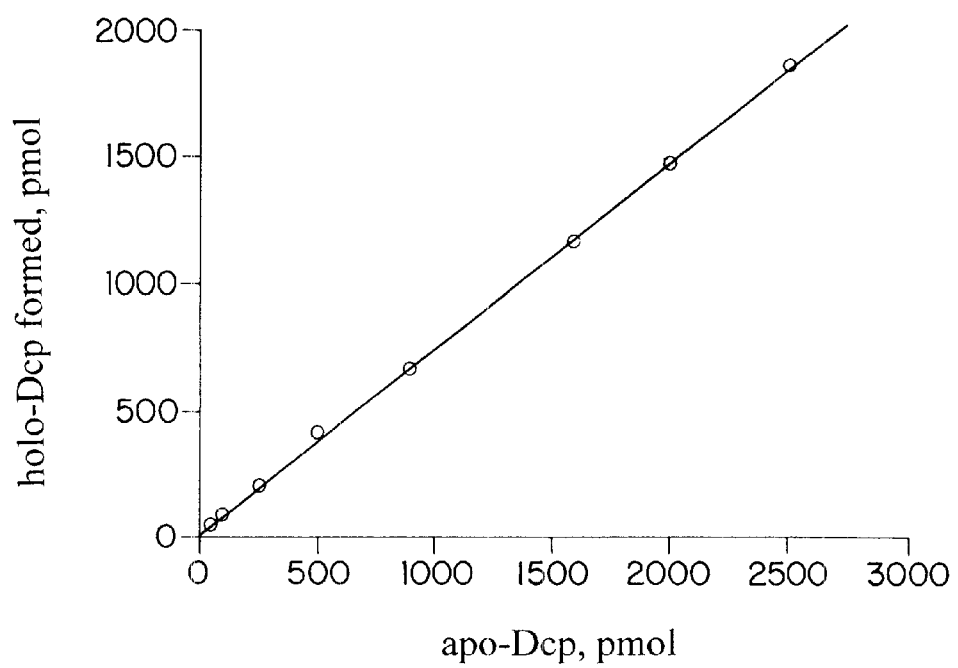
FIG. 4 is a graphic representation of the number of pmol of holo-Dcp formed per number of pmol of apo-Dcp incorporated in an in vitro phosphopantetheinylation reaction with recombinant E. coli ACPS.

The [$^3$H] holo-Dcp formed was quantitated by dividing dpm by specific activity of pantetheinyl moiety of CoA which is equal to 4.83×10$^{14}$ dpm/mol. The results are presented in FIG. 4. These results indicate that the amount of holo-Dcp formed increases linearly with the amount of apo-Dcp in the reaction.

It has also been shown that *E. coli* ACPS modifies the apo-form of Streptomycete ACPs involved in frenolicin, granaticin, oxytetracycline, and tetracenomycin polyketide antibiotic biosynthesis.

Discussion

Wild-type holo-ACP synthase (ACPS) was purified to homogeneity from *E. coli* and the N-terminal peptide sequence was used to identify dpj as the gene which encodes ACPS. ACPS appears to be a homodimer with a native molecular weight of 28,000. Overexpression of dpj has allowed the isolation of >10 mg of active recombinant ACPS. Surprisingly, a first search of the Genbank databases including the recently reported Haemophilus influenzae genome (Fleischmann, R. D., et.al. (1995) *Science* 269:496–512) revealed no known genes which share significant homology with dpj. It is likely that dpj will be useful for the cloning of other phosphopantetheinyl transferases and will assist in the heterologous overproduction of appropriately modified 4'-PP requiring enzymes, such as PhbC (Gerngross, T. U., et al. (1994) *Biochemistry* 33:9311–9320), Dcp (Heaton, M. P. and Neuhaus, F. C. (1994) *J. Bacteriol.* 176:681–690; Perego, M., et al. (1995) *J. Biol. Chem.* 270:15598–15606), TcmM (Shen, B. et al. supra), and NodF (Geiger, O. et al. supra) thereby greatly facilitating the production of acyl activating enzymes involved in macrolide, polyketide, depsipeptide, and non-ribosomal peptide biosynthesis as well as ACP-dependent transacylase activities.

EXAMPLE 2

Identification of Additional Phosphopantetheinylating Enzymes

Figure 7:
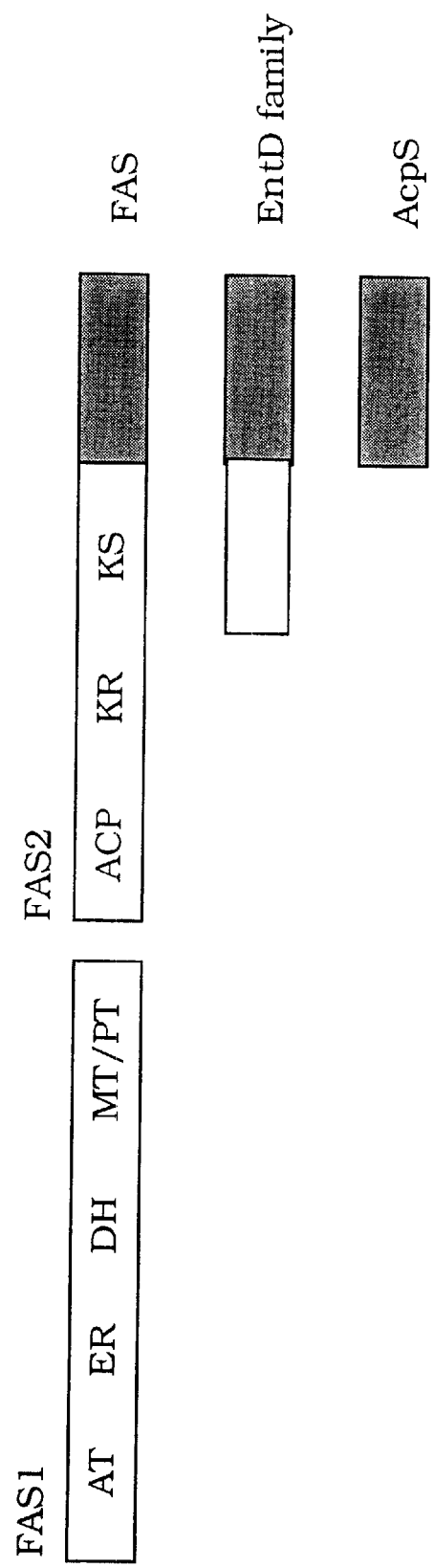
FIG. 7 is a schematic diagram of homologous regions (shaded) among fatty acid synthases (FAS) from S. cervisiae, S. pombe, C. albacans, A. nidulans, and P. patulum, the EntD homology family including Sfp, Gsp, HetI, Lys5, and O195, and E. coli AcpS. Ketoreductase (KR), ketosynthase (KS), acyl transferase (AT), enoyl reductase (ER), dehydratase (DH), and malonyl/palmitoyl transferase (MT/PT).

BLAST searches (Basic Local Alignment Search Tool) (Altschul, S. F. et al. (1990) *J. Mol. Biol.* 215:403–410) with the 125 aa *E. coli* ACPS proteinsequence revealed marginal similarities to the C-terminal region of five fungal fatty acid synthases, suggesting that phosphopantetheinylation activity may have been subsumed as a domain in these polyenzymes (FIGS. 6 and 7). In particular, similarities of 15–22% over 120 residues to the C-terminal region of three fungal fatty acid synthases were found. Genetic evidence supports a scheme in which the C-terminus of the FAS2-subunit could be responsible for the auto-phosphopantetheinylation of the FAS2 N-terminal ACP domain (Kuhn, L. et al. (1972) *Eur. J. Biochem.* 24:492–497; Schweizer, E. et al. (1973) *Eur. J. Biochem.* 39:353–362; Schweizer, E. (1977) *Naturwissenschaften* 64:366–370; Schweizer, E. et al. (1987) *Fat Sci. Technol.* 89:570–577; Werkmeister, K. et al. (1980) *Biochem. Biophys. Res. Comm.* 96:483–490). For example the C-terminal 121 amino acids of the 1894 amino acid (aa) yeast fatty acid synthase subunit II (yFASII) could act intramolecularly to add a P-pant unit to Ser-180, the putative ACP domain of this polyprotein. Schweizer's group has previously reported intrallelic complementation and in vitro reactivation of mutant FAS, one at S180 and one at G1777, which are by themselves inactive, consistent with this proposal (Kuhn, L. et al. (1972) *Eur. J. Biochem.* 24:492; Schweizer, E. et al. (1973) *Eur. J. Biochem.* 39:353; Schweizer, E. (1977) *Naturwissenschaften* 64:366; Schweizer, E., et al. (1987) *Fat Sciences Technology* 89:570; Werkmeister, K. et al. (1980) (1980) *Biochem. Biophys. Res. Commun.* 96:483; Schorr, R. et al. (1994) *J. Plant Physiol.* 143:407).

From the homology between fungal FAS2 C-termini and ACPS, further sequence comparisons revealed homology of *E. coli* ACPS to three bacterial proteins, EntD (*E. coli*), Sfp (*B. subtilis*), and Gsp (*B. brevis*) (FIGS. 6 and 8). The specific biochemical functions of entD, sfp and gsp were unknown. Ent D had been shown to be required for production of the $Fe^{III}$-chelating siderophore enterobactin in *E. coli* (Coderre, P. E. and Earhart, C. F. (1989) *J. Gen. Micorbiol.* 135:3043–3055). Sfp was isolated as a locus required for production of the lipopeptide antibiotic surfactin in *B. subtilis* (Nakano, M. M., et al. (1992) *Mol. Gen. Genet.* 232:313–321). Gsp is a protein required for the synthesis of gramicidin by the multidomainal gramicidin synthase complex GrsAB (Borchert, S. et al. (1994) *J. Bacteriol.* 176:2458). In addition to EntD, Sfp and Gsp further BLAST searches revealed that a third *E. coli* ORF (in addition to ACPS and EntD) of unknown function designated o195 is also homologous to ACPS.

EntD, Sfp, and Gsp have previously been identified as orthologs of high three way homology (Grossman, T. H. et al. (1993) *J. Bacteriol.* 175:6203). In fact, *E. coli* EntD can complement sfp mutants consistent with equivalent functionality (Grossman, T. H. et al. supra; Borchert, S. et al. (1994) *J. Bacteriol.* 176:2458).

FIGS. 6, and 8 show alignments of amino acid sequences of the yeast fatty acid synthases, *E. coli* ACPS, EntD, Sfp, Gsp, and Lpa. These alignments show 2 regions of conserved amino acids in these proteins. In addition to EntD, Sfp, Gsp, and Lpa, further BLAST searches revealed several other proteins which share potential homology with ACPS (FIG. 9), among them a third *E. coli* ORF (in addition to ACPS and EntD) of unknown function designated o195 as well as proteins involved in cyanobacterial heterocyst differentiation and fungal lysine biosynthesis. Local sequence alignments of the putative P-pant transferase domains reveal two sequence motifs containing several highly conserved residues. The highly conserved residues in these regions of homology are boxed in FIG. 9. It is highly likely that these regions are involved in transfer of the phosphopantetheine group. Mutagenesis studies of this domain confirm in fact that the conserved regions are involved in phosphopantetheinyl transfer.

EXAMPLE 3

Sfp, EntD, and o195 Phosphopantetheinylate Substrates in vitro

This example demonstrates that the proteins Sfp, EntD, and o195 shown to have sequence homology to the *E. coli* ACPS are capable of phosphopantetheinylating one or more substrates in vitro. Each of these proteins were overproduced and purified, and were shown to be able to transfer tritium-labeled 4'-Ppant from CoA to the *E. coli* FAS apo-ACP, the apo-ACP domain from the multifunctional peptide synthetase, TycA, EntF, and/or SrfB1, depending on the transferase.

Overproduction and purification of Sfp, EntD, and o195 was performed as follows. Sfp (26.1 kD) was overproduced and purified following previously published procedures (Nakano, M. M. et al. (1992) *Mol. Gen. Genet.* 232).

EntD (23.6 kd) had previously been cloned, but its overproduction had proven difficult, presumably due to the frequency of rare codons and an unusual UUG start codon (Coderre, P. E. & Earhart, C. F. (1989) *J. Gen. Microbiol.* 135:3043). Therefore the UUG start codon was changed to AUG and the codon usage for the first six residues was optimized. EntD was PCR-amplified from wild-type *E. coli* K-12 by colony PCR using the forward primer 5'-ATTATATCCATGGgtTCcTCcGTtTCcAAcATGGT CGATATGAAAACTACGCA-3' (SEQ ID NO: 75) and the reverse primer 5'-GATGTC AAGCTTATTAATCGTGTTGGCACAGCGTTAT-3' (SEQ ID NO: 76)(IDT). The forward primer introduced an NcoI restriction site (underlined) which allowed mutation of the TTG start to an ATG start and inserted a Gly codon (GGT) after the Met initiator. In addition the forward primer optimized codon usage for the first six codons of the entD gene (modified bases shown in lower case). The reverse primer incorporated a HindIII restriction site (underlined). The NcoI/HindIII digested PCR product was cloned into pET28b (Novagen) and transformed into competent *E. coli* DH5α. Competent cells of the overproducer strain *E. coli* BL21 (DE3) were then transformed with the supercoiled pET28b-entD plasmid. Induction of a 2 L culture BL21 (DE3) pET28b-entD with 1 mM IPTG followed by growth at 25° C. for 5 hours yielded predominantly inclusion bound EntD, however a modest amount of the overproduced protein was soluble. The induced cell paste was resuspended in 50 mM Tris, 1 mM EDTA, 5% glycerol, pH 8.0 (40 mL) and lysed by two passages through the French press at 15,000 psi. Cellular debris and inclusion bound protein was removed by centrifugation at 8,000×g for 30 minutes. Pulverized ammonium sulfate was added to 35%, 65% and 80% saturation. The 35% fraction containing the largest fraction of EntD was applied to a 2.5×115 cm Sephacryl S-100 column. The column was eluted at a flow rate of 1 mL/min using the same buffer as above collecting 8 mL fractions to obtain homogeneously pure EntD.

Similarly, o195 (Sofia et al. (1994) *Nucleic Acids Research* 22:2576–2586) was PCR amplified from wild-type *E. coli* K-12 by colony PCR using the forward primer 5'-ATTATATCCATGGgtTAcCGGATAGTTCTGGGGA AAGTT-3' (SEQ ID NO: 77) and the reverse primer 5'-TGATGTC AAGCTTATCAGTTAACTGAATCGATCCATTG-3' (SEQ ID NO: 78)(IDT). The forward primer with its NcoI restriction site (underlined) gave insertion of a Gly codon (GGT) after the Met initiator codon of the o195 sequence. Codon usage for the succeeding codon was also optimized (base change shown in lower case). The reverse primer incorporated a HindIII restriction site (underlined). The NcoI/HindIII-digested PCR product was cloned into pET28b (Novagen) and transformed into competent *E. coli* DH5α. Competent cells of the overproducer strain *E. coli* BL21 (DE3) were then transformed with the supercoiled pET28b-o195 plasmid. Induction of a 2 L culture (2×YT media) of BL21(DE3)pET28-o195 with 1 mM IPTG followed by growth at 37° C. for 3.5 h yielded predominantly inclusion-bound o195 protein. The cell paste was resuspended in 50 mM Tris.HCl, 1 mM EDTA, 5% glycerol, pH 8.0 (40 mL) and lysed by two passages through a French pressure cell at 15,000 psi. Cellular debris and inclusion-bound protein was pelleted by centrifugation at 27,000×g for 30 minutes (min.). The inclusion-bound protein pellet was resuspended in 30 mL of 50 mM Tris.HCl, pH 8.0, 1 mM EDTA, and 5% glycerol and incubated for 30 minutes at room temperature with 10 mg lysozyme and 30 mg deoxycholate. The pellet was reobtained by centrifugation for 15 min at 27,000×g and solubilized in 30 mL of 8 M urea, 50 mM Tris.HCl, pH 8.0, 10 mM DTT. Residual solid material was removed by centrifugation for 15 min at 27,000×g. The urea-solubilized solution (30 mL) was then applied to a 2.5×10 cm Q-Sepharose column equilibrated with 8 M urea, 50 mM Tris.HCl, pH 8.0. The column was washed with 50 mL of the equilibration buffer and then a gradient of 250 mL 0–0.25 M NaCl in 8 M urea, 50 mM Tris.HCl pH 8.0 followed by 200 mL of 0.25–1 M NaCl in the same buffer was applied. The o195 protein eluted at approximately 200 mM NaCl as determined by 15% SDS-PAGE. The purified o195 was renatured by diluting a portion of it 10-fold in 8 M urea, 50 mM Tris.HCl, pH 8.0, 10 mM DTT and dialyzing overnight at 4° C. against 10 mM Tris.HCl, pH 8.0, 1 mM DTT. Two liters of culture grown in 2×YT media yielded 3.1 g of cells from which approximately 80 mg of o195 protein was obtained.

The substrates were overexpressed and purified as follows. The *E. coli* fatty acid synthase ACP was overproduced and purified in its apo-form from *E. coli* strain DK554 (Crosby, J. et al. (1995) *Biochemica et Biophysica Acta* 1251:32) following the procedure of Rock and Cronan (Rock, C. O. & Cronan, J. E., Jr. (1981) *Methods Enzymol.* 71:341–351) with the exception that following cell disruption and centrifugation (30 min at 28,000×g), the crude extract containing 10 mM $MgCl_2$ and 10 mM $MnCl_2$ was incubated for 60 min at room temperature. In this manner, minor amounts of holo-ACP were hydrolyzed to the apo-form using the endogenous *E. coli* ACP phosphodiesterase (Fischl, A. S. & Kennedy, E. P. (1990) *J. Bacteriol.* 172, 5445–5449).

Figure 10:
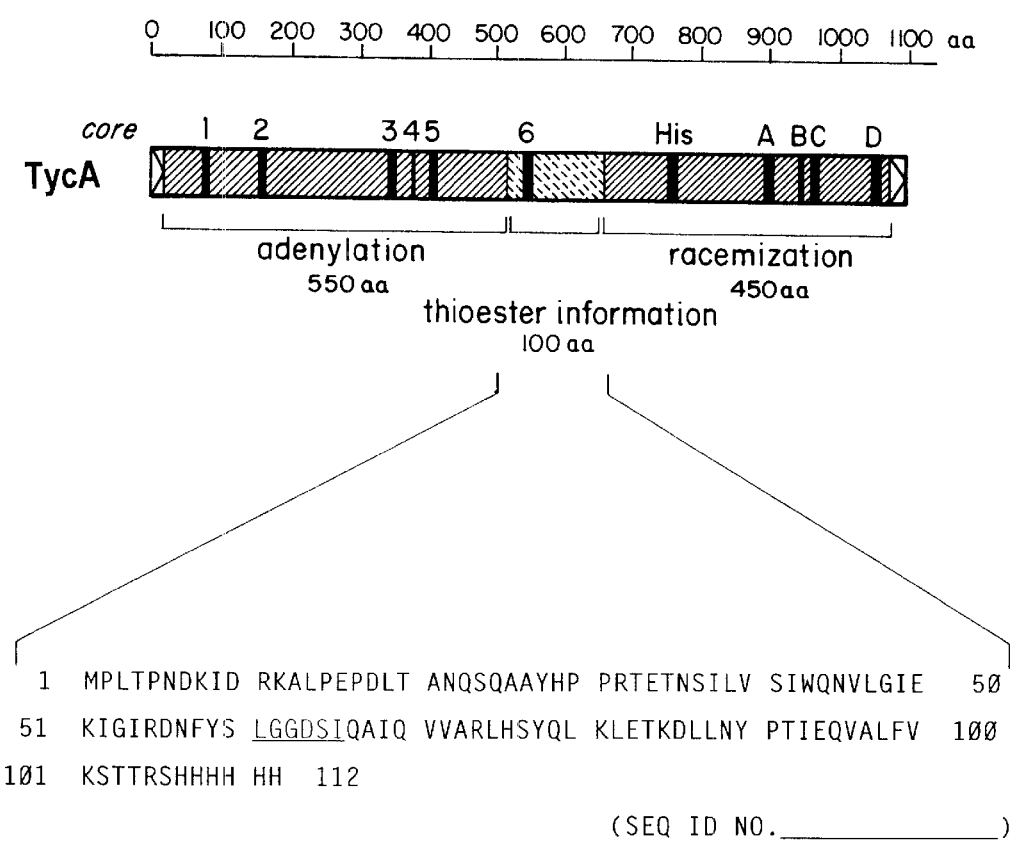
FIG. 10 is a schematic diagram of the protein TycA and the region of 112 amino acids from TycA (SEQ ID NO:56) used for preparing the substrate His6-peptidyl carrier protein (His6-PCP).

The peptidyl carrier protein (PCP) domain of TycA (FIG. 10) was overproduced with a hexa-histidine tag using *E. coli* strain SG13009(pREP4)/pQE60-PCP (Stachelhaus et al. (1996) *Chemistry & Biology,* vol. 3(11), 913–921). Following lysis of the induced culture the $His_6$-tagged protein was purified by nickel-chelate chromatography.

Apo-SrfB1 was cloned from plasmid p120-21E (Nakano, M. M. et al. (1991) *J. Bacteriol.* 173:1770–1778). Briefly, p120-21E was digested with EcoRV to release a 3,648 base pair fragment encoding the SrfB1, valine-activating domain of surfactin synthetase. This fragment was inserted into StuI-cleaved pPROEX-1 (Gibco/BRL Life Sciences Technologies) to give plasmid pML118 which codes for a N-terminal hexa-hisitidine-tagged SrfB1 domain (142.7 kD). His6-SrfB1 was overproduced using *E. coli* strain AG1574 (Frisby, D. & Zuber, P. (1991) *J. Bacteriol.* 173:7557–7564). Cells were grown at 25° C. in 2×YT media (2 L) to an O.D. of 0.4 at which point they were induced with 1 mM IPTG and allowed to grow for an additional 4 hours. Cells were harvested by centrifugation (3 g), resuspended in 35 mL of 5 mM imidazole, 500 mM NaCl, 20 mM Tris.HCl, pH 7.9 and lysed by two passages through a French pressure cell. This crude extract was clarified by centrifugation for 30 min at 27,000×g. More than 50% of the overexpressed SrfB1 was obtained in the soluble fraction as determined by 6% SDS-PAGE. Hexa-histidine tagged SrfB1 was purified on His-Bind resin (Novagen) following the manufacturer's recommendations.

EntF was overproduced and purified as described in Keating, D. H. et al. (1995) *J. Biol. Chem.* 270:22229 and Reichert, J. et al. (1992) *Prot. Sci.* 1:549.

Phosphopantetheinyl transferase activity toward a substrate was assayed by monitoring the transfer of [$^3$H]-4'-phosphopantetheine from [$^3$H]-(pantetheinyl)-CoASH in the presence of the putative P-pant transferase enzyme by radioassay. Enzyme preparations were incubated with 75 mM Tris.HCl, pH 8.5, 10 mM MgCl2, 5 mM DTT, 160 $\mu$M [3H]-(pantetheinyl)-CoA, 25 $\mu$M ACP or His6-PCP for 60 min at 37° C. in a final volume of 100 $\mu$L. The incubations were quenched with 10% TCA and 500 $\mu$g BSA was added as a carrier. The protein was precipitated by centrifugation, washed 3× with 10% TCA, and the protein pellet was solublized with 150 $\mu$L 1 M Tris base. The resuspended protein was added to 3 mL liquid scintillation cocktail and the amount of [3H]-phosphopantetheine incorporated into the substrate protein was quantified by liquid scintillation counting.

Specific covalent attachment of 4'-Ppant to the ACP and His6-PCP substrates was confined by autoradiography. These assays were performed as described above except 20 $\mu$M [$^3$H]-(pantetheinyl)-CoASH (2.6×10$^6$ dpm total activity) was used in the assay, no BSA was added to the TCA precipitate, and pellets were solubilized in SDS or native PAGE sample buffer titrated with 1 M Tris base. Assays using apo-PCP as substrate were resolved by 15% SDS-PAGE, assays using *E. coli* ACP were resolved by 20% native PAGE, and assays using SrfB1 or EntF were resolved on 8% SDS-PAGE. Gels were Coomassie-stained, soaked 30 minutes in Amplify (Amersham), dried at 80° C. under vacuum and exposed to X-ray film for 24 to 150 hours at –70° C. The autoradiograms were scanned using a digital scanner and relative intensities of the radiolabeled bands were quantified using NIH Image 1.59 software (National Institutes of Health, USA).

Figure 11:
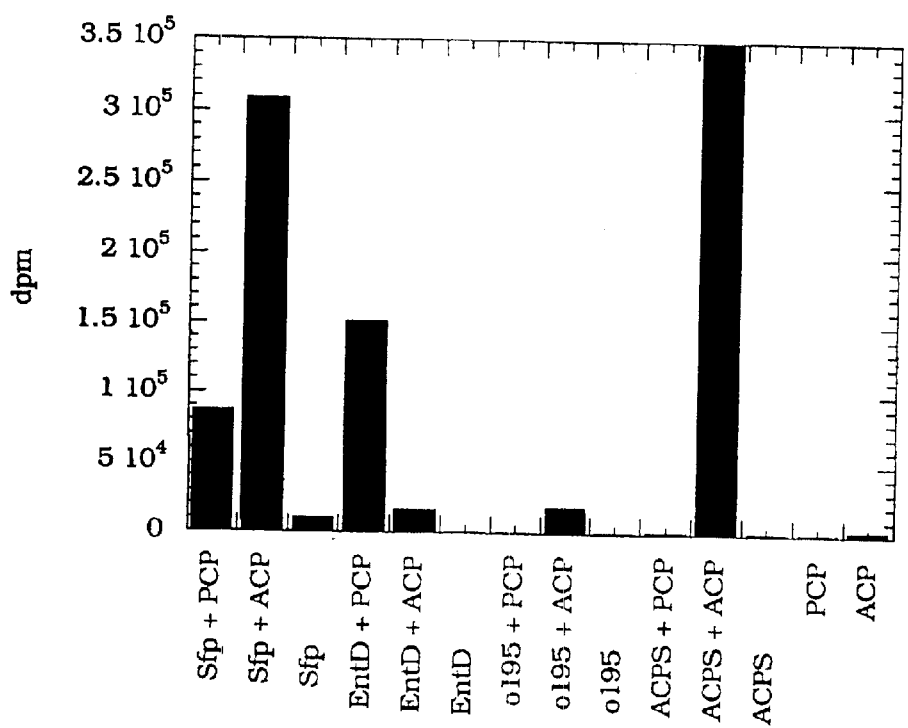
FIG. 11 represents a histogram showing Sfp, EntD, and o195 mediated incorporation of [3H]-4'-Ppant into ACP and His6-PCP.

The results of the phosphopantetheinylation assays performed in the presence of Sfp, EntD, or o195 are presented in FIG. 11. These results show that Sfp, EntD and o195 are capable of transferring phosphopantetheine groups to a substrate as ACP and His6-PCP. It was further shown that [3H]-phosphopantetheine is in fact specifically and covalently attached to ACP and His6-PCP following the phosphopantetheinylation reaction mediated by Sfp, EntD, or o195.

Figure 12:
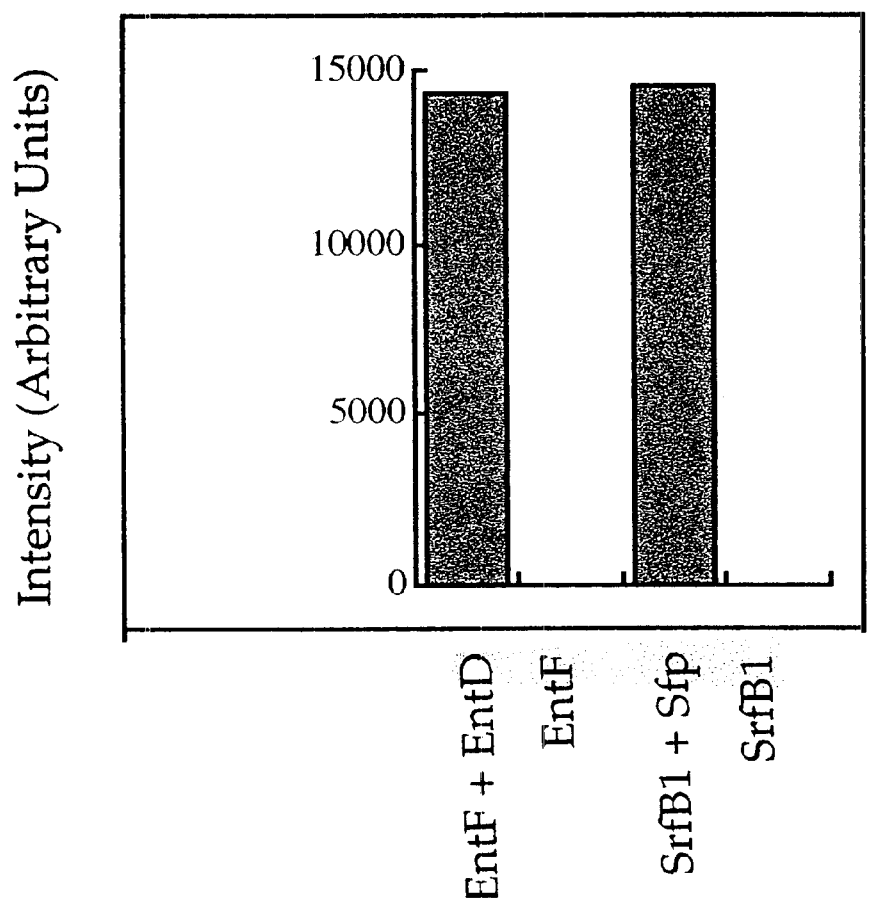
FIG. 12 represents a histogram showing EntD and Sfp mediated incorporation of [3H]-4'-Ppant into EntF and SrfB1, respectively.

FIG. 12 shows that EntD is capable of phosphopantetheinylating an EntF fragment and Sfp is capable of phosphopantetheinylating an SfrB1 fragment.

Further confirmation that the tritium radioactivity incorporated into the apo-proteins represented transfer of the intact phosphopantetheinyl group was assessed by mass spectrometry (Lambalot, R. H. and Walsh, C. T. (1995) *J. Biol. Chem.* 270:24658). Mass spectrometric analysis (MALDI-TOF) of unlabeled enzymatic holo-PCP indicated a molecular weight of 13,431 (calculated 13,459) in contrast to an observed molecular weight of 13,130 (calculated 13,120) for the apo-PCP substrate. Thus, these data establish that EntD, Sfp, and o195 are enzymes that catalyze the transfer of P-pant to the serine side chain of an acyl carrier protein.

For the determination of Km for apo-ACP and His6-PCP using Sfp, the linear range of the assay was determined by monitoring the percentage conversion of apo-substrate to holo-substrate versus time at various enzyme concentrations using the radioassay described above. Having determined the linear range of the assay, the initial velocity of phosphopantetheinyl transfer was measured using a fixed concentration of Sfp and varying the concentration of the substrate (ACP or His6-PCP).

Figure 13:
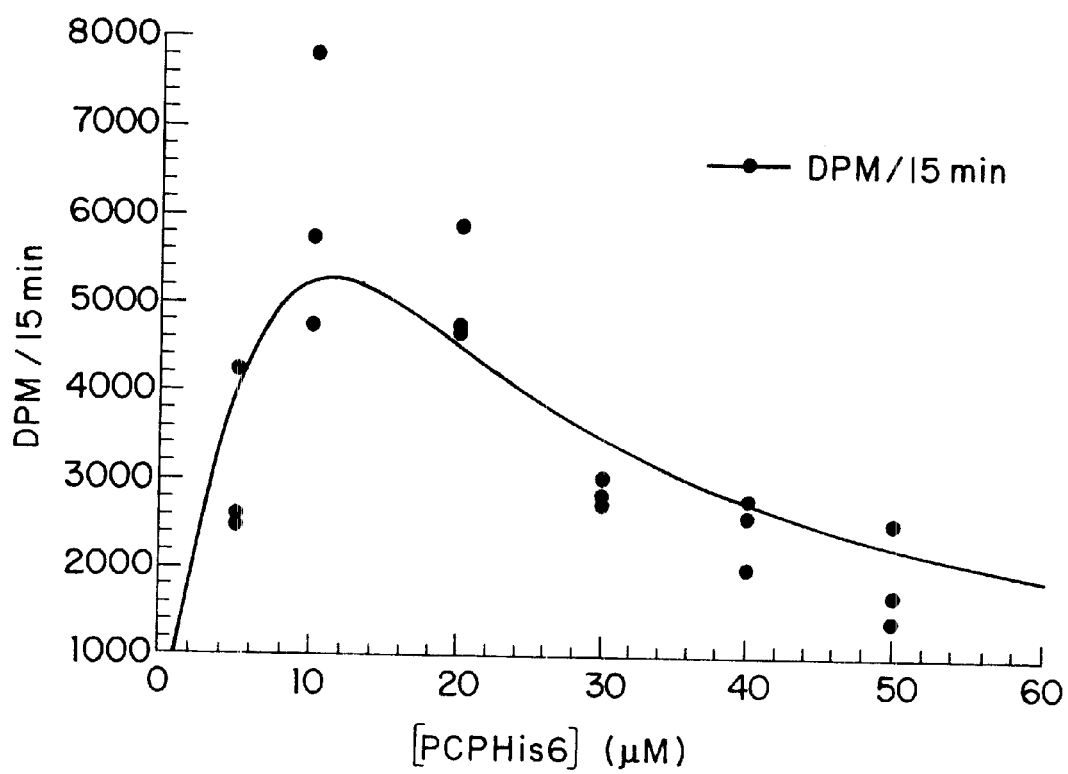
FIG. 13 is a graphical representation of the amount of [3H]-4'-Ppant incorporated into PCP-His6 during a 15 minute reaction with 13 nM Sfp and different concentrations of the substrate.

The results are presented in FIG. 13. These show that Sfp is capable of phosphopantetheinylating a substrate, such as PCP, in a wide range of concentrations.

Figure 14:
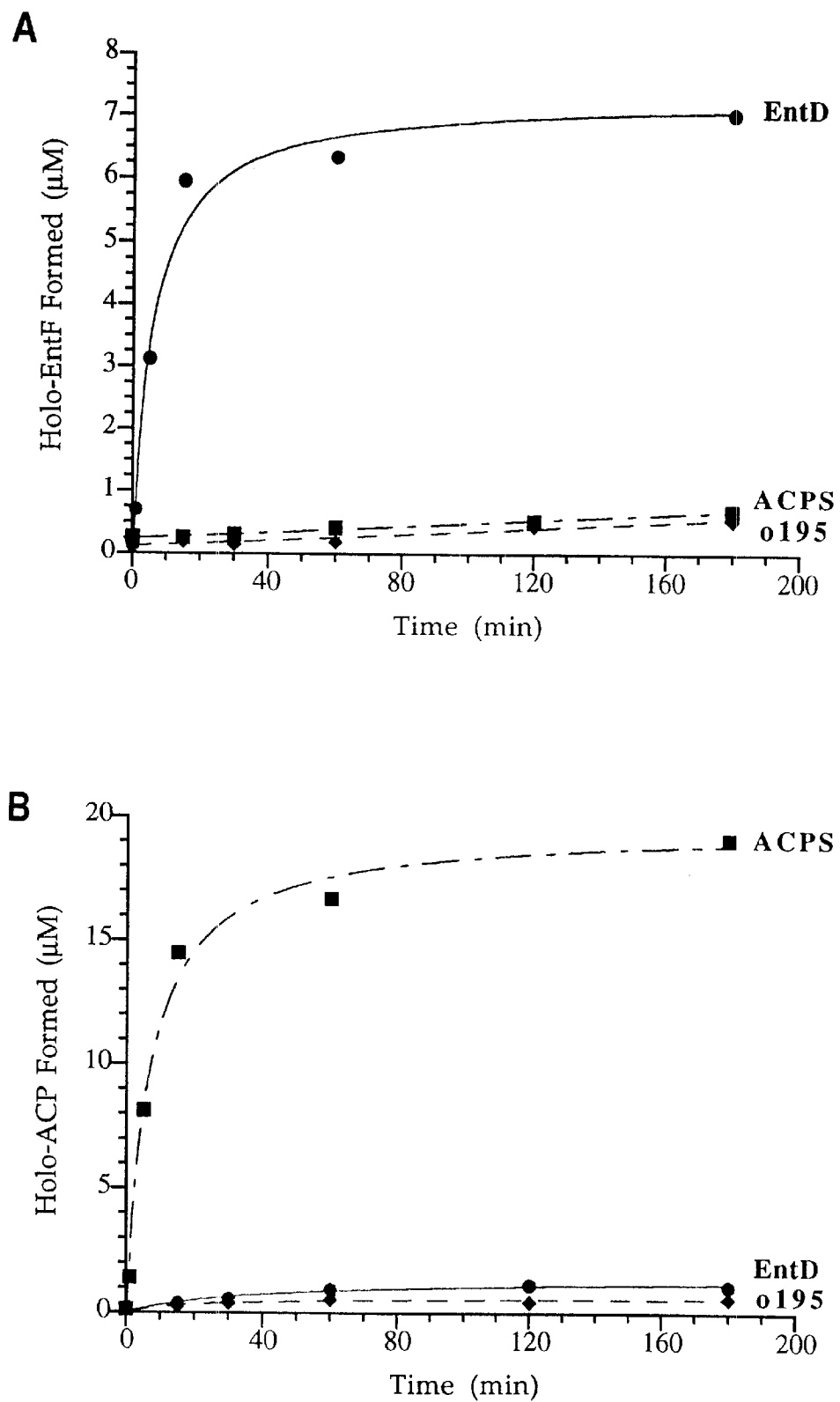
FIG. 14 Panel A is a diagram representing the amount of Holo-EntF formed as a function of time upon incubation of Apo-EntF with EntD, ACPS, or o195.

A time course of EntD-catalyzed incorporation of radiolabel into EntF was performed. As shown in FIG. 14A, EntF is modified effectively by EntD (100 nM), whereas EntF undergoes almost no modification in the presence of 15-fold higher concentrations of ACPS and o195, clearly demonstrating the specificity of EntD for EntF. In contrast, FIG. 14B shows almost exclusive modification of apo-ACP by ACPS, confirming that ACPS is the P-pant transferase which activates the type II fatty acid synthase and EntD is the P-pant transferase which activates the type I enterobactin synthetase in *E. coli*.

Thus, this analysis provided in vitro evidence of at least two partner-specific P-pant transfer reactions occurring within *E. coli*: ACPS specifically catalyzes transfer of P-pant to apo-ACP while EntD is the partner transferase for EntF. o195 is likely to has a unique specificity for a third unknown substrate in *E. coli*. It is likely that P-pant transfer to this unknown protein would be catalyzed efficiently only by o195 and not by ACPS or EntD. One possible partner for o195 is the unknown 35 kDa protein in *E. coli* which has been observed to incorporate [$^3$H]β-alanine in vivo (Gerngross, T. U. et al. (1994) *Biochemistry* 33:9311).

Sfp, on the other hand, would appear to be non-specific with respect to the two Bacillus derived type I peptide synthetase domains, PCP and SrfB1, and the *E. coli* type II fatty acid synthase ACP subunit. As shown above, Sfp efficiently catalyzes modification of all three substrates and in addition can catalyze modification of EntF. Based on this evidence, Sfp would appear not to discriminate between type I peptide synthetase domains and type II fatty acid subunits suggesting that there may be cross-talk between Sfp and fatty acid synthase at least when expressed in *E. coli*.

The establishment of phosophopantetheinyl transfer activity for Sfp in the studies described here clearly assigns a catalytic loading function to Sfp for posttranslational modification of the conserved serine in the first subsite of SrfB responsible for valine activation. The srf operon consists of four open reading frames in which srfA, srfb, and srfC encode for the activities that activate and assemble the seven component amino acids and branded chain β-hydroxy fatty acid of surfactin. It is likely that Sfp is able to modify the consensus serine residue in all seven amino acid activating sites in SrfABC.

By extension, Gsp is responsible for the posttranslational modification of the five amino acid activating sites in GrsA and GrsB, allowing for the sequential activation and polymerization of amino acids in the thiotemplate mechanism for non-ribosomal peptide bond assembly.

Likewise, demonstration of 4'-phosphopantetheinyl (4'-Ppant) transferase activity in EntD assigns a biochemical function to EntD. EntF, a 140 kDa component in the pathway had previously been cloned, sequenced, and purified and shown to activate L-serine and to contain phosphopantetheine (Rusnak, F. et al. (1991) *Biochemistry* 30:7740). Given that EntD is required for enterobactin biosynthesis in vivo and, as set forth above, shows high activity for in vitro P-pantetheinylation of pure apo-EntF, EntD can be defined as the specific P-pant transferase that makes active holo-EntF from apo-EntF in vivo. Pure *E. coli* ACPS will not significantly posttranslationally modify EntF, consistent with the hypothesis that protein-protein recognition controls the specificity of phosphopantetheinylation in vivo. It is likely, that incubations of EntD and the enterobactin synthetase components with CoASH. L-serine and dihidroxybenzoate reconstitute in vitro enterobactin production. At 140 kDa, EntF is the typical size of an aa-activating module in multidomain polypeptide synthetases (Stachelhaus, T. & Marahiel, M. A. (1995) *FEMS Microbiol. Lett.* 125:3). Its efficient modification in vitro by EntD shows that P-pant addition can occur after translation of the apo-protein rather than exclusively co-translationally prior to folding of the apo-protein into its native structure. The NMR structure of *E. coli* apo-ACP shows the nucleophilic Ser-36 is in an accessible β-turn (Holak, T. A. et al. (1988) *Eur. J. Biochem.* 175:9), possibly a common architectural scaffolding for ACP domains in polyketide and polypeptide synthases which may play a role in recognition by P-pant transferases.

The genetics argue strongly for specific partner peptide synthetase recognition by a given posttranslational modification enzyme and this may well be a general theme in non-ribosomal peptide antibiotic biosynthesis. It has been previously observed that pure *E. coli* ACP synthase will not posttranslationally modify EntF, consistent with protein-protein recognition to control specificity.

EXAMPLE 4

Holo-SrfB1 is Competent for Activation of its Cognate Amino Acid, L-valine.

This Example shows that holo-SrfB1 produced in vitro from modification of apo-SrfB1 with Sfp is competent for activation of its cognate amino acid, L-valine.

The reaction was performed as follows. Apo-SrfB1 (2 μM) was incubated with 200 μM CoASH, 75 mM Tris.HCl pH 8.0, 10 mM MgCl$_2$, 25 mM DTT and 1.3 μM Sfp for 15 min at 37° C. to generate holo-SrfB1. To the SrfB1-Sfp reaction mixture, unlabeled amino acid (valine or aspartic acid) was added to 90 μM final concentration. ATP was added to a final concentration of 2 mM, followed by 0.5 μCi [$^{14}$C]Val (281 Ci/mol) or [$^{14}$C]Asp (207 Ci/mol). The reaction (115 μL) was incubated for 15 min at 37° C., then stopped by the addition of 800 μL 10% TCA with 15 μL of a 25 mg/mL BSA solution as carrier. The precipitate was collected by centrifugation, washed with 10% TCA, dissolved in 150 μL Tris base, and then counted by liquid scintillation.

Figure 15:
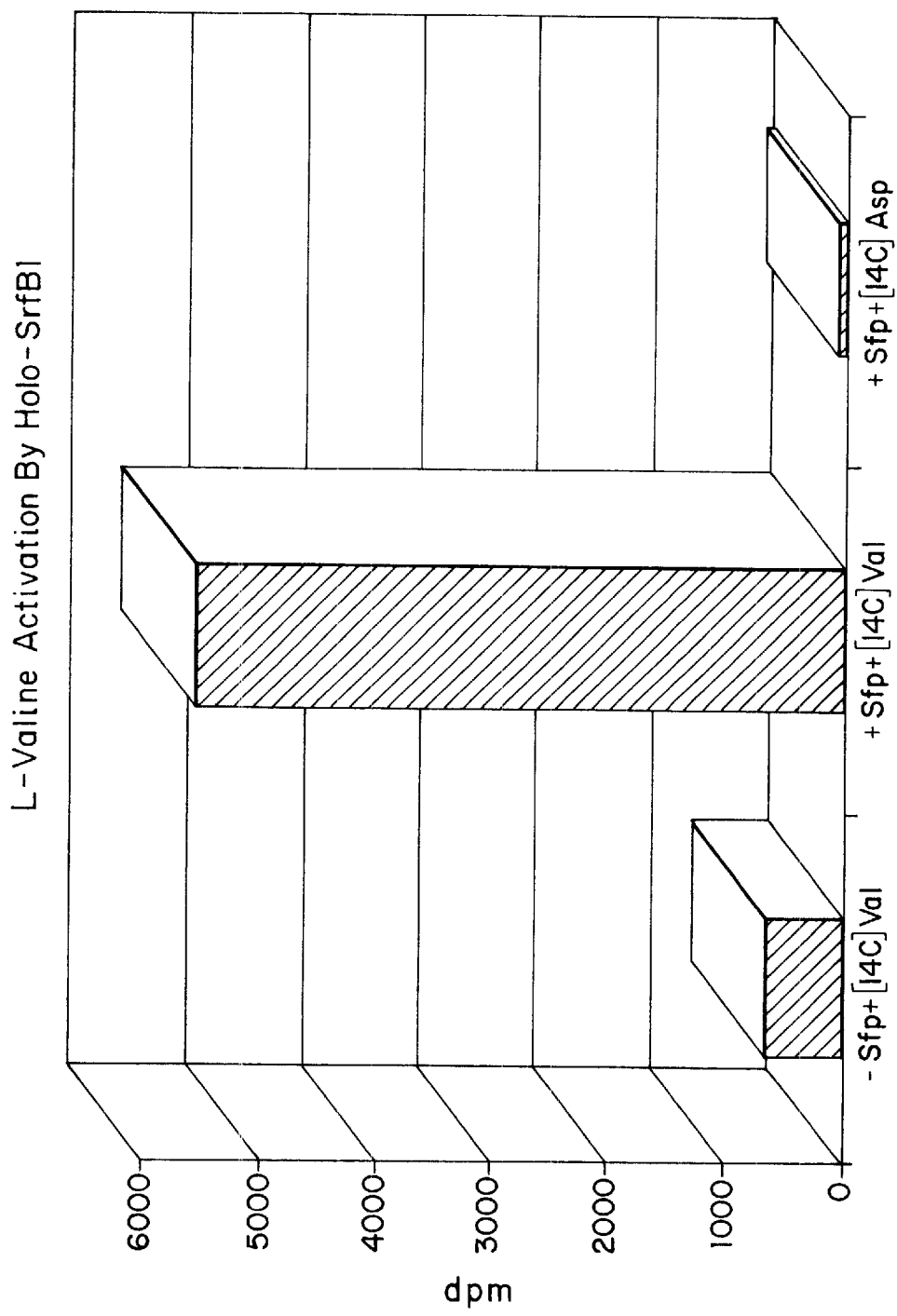
FIG. 15 is a histogram representing the extent of $[^{14}C]$ Valine activation by holo-SrfB1 preincubation of SrfB1 with CoA in the absence of Sfp (–Sfp+[14C]Val) or in the presence of Sfp (+Sfp+[14C]Val) before subsequent incubation with $[^{14}C]$-L-Valine, or in the presence of Sfp before subsequent incubation with $[^{14}C]$-L-Aspartate and ATP (+Sfp+[14C] Asp).

The results are presented in FIG. 15. The histogram presented in this figure shows that apo-SrfB1 undergoes very little acylation when incubated with [$^{14}$C]-L-valine indicating a small amount of contamination by holo-SrfB1. However, following incubation with Sfp the level of [$^{14}$C]-L-valine-holo-SrfB1 covalent complex formed in the complete incubation mixture increases about 14-fold, consistent with an increase in the amount of holo-SrfB1 present. This arises from valyl-AMP formation by the amino acid-activating domain of holo-SrfB1 followed by intramolecular acyltransfer to the SH group of the P-pant moiety in the adjacent PCP domain. Finally, holo-SrfB1 cannot be covalently acylated by the non-cognate L-aspartate residue, the fifth amino acid to be activated by SrfABC, consistent with the absence of an aspartate specific adenylation domain on SrfB1.

Thus, this Example shows that the holo-SrfB1 formed following incubation with Sfp and CoASH has both an active adenylation domain and a functional holo-peptidyl carrier protein domain. Furthermore, it shows that the action of Sfp on the 143 kD SrfB1 fragment in conversion of the apo to holo-form generates a phosphopantetheinylated SrfB1 competent to undergo specific recognition and acylation by the amino acid L-valine, residue 4 in surfactin. Sfp and other phosphopantetheinyl transferases should therefore be useful reagents, e.g., to probe peptide bond-forming steps between adjacent sites of multienzyme, multiple thiotemplate synthases.

EXAMPLE 5
Identification of Additional Phosphopantetheinylating Enzymes

Using the EntD/Sfp/Gsp family as a base for further database searches has led to the identification of several additional candidates that are likely 4'-P-pant transferase family members (Table IV and FIG. 9). A hypothetical protein, HIO152, in *H. influenzae* has been identified as a putative P-pant transferase thereby satisfying the apparent lack (using ACPS-based searches) of a P-pant transferase in the Haemophilis genome. HIO152 is positioned directly upstream of the *H. influenzae* fatty acid synthase gene cluster, consistent with a function for its protein product in fatty acid biogenesis. Also identified in Table IV and FIG. 9 are two additional proteins in cyanobacteria and in yeast for which prior genetic evidence accords with the putative functions proposed herein. In Anabaena, the genes HetI, HetM, and HetN have been implicated in the production of a proposed secondary metabolite which inhibits heterocyst differentiation, a process occurring under low fixed nitrogen conditions in which a subset of cyanobacterial cells differentiate into the specialized heterocysts which have the ability to fix nitrogen (Black, T. A. & Wolk, C. P. (1994) *J. Bacteriol.* 176:2282). Sequence analysis suggests HetN is a NAD(P)H-dependent oxidoreductase such as those involved in the biosynthesis of polyketides and fatty acids while HetM has an ACP domain. HetI, with its similarity to Sfp/Gsp/EntD, is thus likely to be the HetM-specific phosphopantetheinyl transferase in the synthesis of the hypothesized secondary metabolite.

Another candidate of the phosphopantetheinylating family of enzymes is the 272 amino acid Lys5 protein involved in the yeast lysine biosynthetic pathway. Yeast and other fungi synthesize lysine via the unique α-aminoadipate pathway, an eight-step pathway beginning with homocitrate and proceeding via α-aminoadipate to saccharopine to lysine (Bhattacharjee, J. K. (1985) *CRC Critical Reviews in Microbiology* 12:131). Genetic analysis has implicated Lys2 and Lys5 by complementation to be involved in the same step in this pathway, the reduction of α-aminoadipate to aminoadipate semialdehyde (Storts, D. R. & Bhattacharjee, J. K. (1989) *Biochem. Biophys. Res. Commun.* 161:182). This reaction appears to proceed through an α-aminoadipoyl-AMP intermediate as indicated by labeled pyrophosphate exchange experiments (Sagisaka, S. & Shimura, K. (1960) *Nature* 188:1191; Sinha, A. K. & Bhattacharjee, J. K. (1971) *Biochem. J.* 125:743). Recent sequence analysis (Morris, M. E. & Jinks-Robertson, S. (1991) *Gene* 98:141) shows Lys2 to be a 155 kDa protein with homology to amino acid-activating peptide synthetases including TycA, GrsAB, and SrfA. Analogous to these peptide synthetases, Lys2 is believed to cleave ATP to AMP and PPi thereby activating α-aminoadipate as the α-aminoacyl-AMP which is then reduced by NADPH to the aldehyde. A search for a consensus P-pant attachment site in Lys2 reveals the signature motif LGGHS around Ser-880. Therefore, it is likely that Lys2 and Lys5 form a two subunit enzyme (Storts, D. R. and Bhattacharjee, J. K. (1989) *Biochem. Biophys. Res. Commun.* 161:182), that the 272 aa Lys5 is a specific phosphopantetheinyl transferase for Ser-880 in Lys2. The thiol of the newly-introduced P-pant prosthetic group on Lys2 would attack the aminoadipoyl-AMP to give aminoadipoyl-S-pant-Lys2, in close analogy to sequential formation of aminoacyl-AMP to aminoacyl-S-pant-TycA in the homologous tyrocydine synthetase A subunit. At this point, hydride addition to the acyl-S-pant-Lys2 would yield a thiohemiacetal which would readily decompose to aldehyde product and HS-pant-Lys2. This sequence has precedent in the reverse direction in the oxidation of glyceraldehyde-3-P to the acyl-S-enzyme in GAP dehydrogenase catalysis via a cysteinyl-S-enzyme hemithioacetal (Walsh, C. T. (1979) *Enzymatic Reaction Mechanisms.* W. H. Freeman and Company, New York).

The bli and lpa-14 gene products most likely play an equivalent role, iterative P-pantetheinylation of each aa-activating domain in *B. licheniformis* bacitracin synthetase (Gaidenko, T. A., et al. (1992) *Biotechnologia* 13) and *B. subtilis* iturin A synthetase respectively (Huanig, C.-C. et al. (1993) *J. Ferment. Bioeng.* 76:445).

TABLE IV

ACP Synthase Homologs

| pathway | gene | organism | protein size |
|---|---|---|---|
| Surfactin Biosynthesis | Sfp | *B. subtilis* | 224 aa |
|  | Psf-1 | *B. pumilus* | 233 aa |
| Iturin A Biosynthesis | Lpa-14 | *B. subtilis* | 224 aa |
| Gramicidin S Biosynthesis | Gsp | *B. brevis* | 237 aa |
| Enterobactin Biosynthesis | EntD | *E. coli* | 209 aa |
|  |  | *Salmonella typhimurium* | 232 aa |
|  |  | *Salmonella austin* | 232 aa |
|  |  | *Shigella flexneri* | 209 aa |
| Heterocycst Differentiation | HetI | *Anabaena sp.* | 237 aa |
|  | SYCCPNC | *Synechocystis sp.* | 246 aa |
| Lysine Biosynthesis | LYS5 | *S. cerevisiae* | 272 aa |
| Fatty Acid Biosynthesis | AcpS (Dpj) | *E. coli* | 126 aa |
|  | HI0152 | *H. influenzae* | 235 aa |
|  | FAS2 | *S. cerevisiae* | 1894 aa |
|  |  | *Candida albicans* | 1885 aa |
|  |  | *Penicillium patulum* | 1857 aa |
|  |  | *S. pombe* | 1842 aa |
|  |  | *Emericella nidulans* | 1559 aa |
| Bacitracin | Bli | *B. licheniformis* | 225 aa |
| Nosiheptide | NshC | *S. actuosis* | 253 aa |
| Proteins of Unknown Function | o195 | *E. coli* | 195 aa |
|  | 1314154 | *S. pombe* | 258 aa |
|  | CELTO4G9 | *C. elegans* | 297 aa |

Thus, these results provide evidence for the existence of a family of more than a dozen proteins with catalytic posttranslational modification activity. It is likely, that there are P-pantetheinyl transferases having CoASH as a common substrate, but that they show specificity, directed by protein-protein interactions, for the conserved serine motif in specific partner proteins. It is further likely that most if not all of the multienzyme peptide synthetases that use the multiple thiotemplate scaffolding to make peptide antibiotics nonribosomally will follow this paradigm of a specific posttranslational modifying enzyme to covalently arm the swinging arm thiol group required to enable acyl transfers. Compared to the 126 amino acid *E. coli* subunit of ACPS, the phosphopantetheinyl transferase homologs shown in FIGS. 6, 8, and 9 have an extra 50–150 amino acid residues which may be specificity-conferring regions for partner proteins.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for phosphopantetheinylating a substrate in a cell or increasing phosphopantetheinylation of a substrate in a cell, wherein the cell is an *E. coli* cell or a yeast cell, comprising transforming the cell with a first nucleic acid molecule comprising an expressible form of a nucleotide sequence encoding a phosphopantetheinyl transferase, wherein the phosphopantetheinyl transferase is *E. coli* acyl carrier protein synthase that comprises the amino acid sequence set forth in SEQ ID NO:10 or a fragment thereof retaining phosphopantetheinylating activity, and a second nucleic acid molecule comprising an expressible form of a nucleotide sequence encoding a protein which is a substrate of the phosphopantetheinyl transferase, wherein the substrate is selected from the group consisting of *Lactobacillus casei* D-Alanyl carrier protein (Dcp) and *E. coli* acyl carrier protein (ACP), such that phosphopantetheinylation of the substrate in the cell occurs or is increased.

2. A method for phosphopantetheinylating a substrate in a cell or increasing phosphopantetheinylation of a substrate in a cell, wherein the cell is an *E. coli* cell or a yeast cell, comprising transforming the cell with a first nucleic acid molecule comprising an expressible form of a nucleotide sequence encoding a phosphopantetheinyl transferase, wherein the phosphopantetheinyl transferase is *Bacillus subtilis* Sfp that comprises the amino acid sequence set forth in SEQ ID NO:8 or a fragment thereof retaining phosphopantetheinylating activity, and a second nucleic acid molecule comprising an expressible form of a nucleotide sequence encoding a protein which is a substrate of the phosphopantetheinyl transferase, wherein the substrate is selected from the group consisting of *Bacillus subtilis* surfactin synthetase B1 domain (SrfB1), *E. coli* acyl carrier protein (ACP) and peptidyl carrier protein (PCP) domain of *E. coli* TycA, such that phosphopantetheinylation of the substrate in the cell occurs or is increased.

3. A method for phosphopantetheinylating a substrate in a cell or increasing phosphopantetheinylation of a substrate in a cell, wherein the cell is an *E. coli* cell or a yeast cell, comprising transforming the cell with a first nucleic acid molecule comprising an expressible form of a nucleotide sequence encoding a phosphopantetheinyl transferase, wherein the phosphopantetheinyl transferase is *E. coli* EntD that comprises the amino acid sequence set forth in SEQ ID NO:9 or a fragment thereof retaining phosphopantetheinylating activity, and a second nucleic acid molecule comprising an expressible form of a nucleotide sequence encoding a protein which is a substrate of the phosphopantetheinyl transferase, wherein the substrate is selected from the group consisting of *E. coli* EntF, *E. coli* acyl carrier protein (ACP) and peptidyl carrier protein (PCP) domain of *E. coli* TycA, such that phosphopantetheinylation of the substrate in the cell occurs or is increased.

* * * * *

SEQUENCE LISTING (1) GENERAL INFORMATION:

(iii) NUMBER OF SEQUENCES: 78

(2) INFORMATION FOR SEQ ID NO:1:

(i) SEQUENCE CHARACTERISTICS:
       (A) LENGTH: 120 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO:1:

```
Lys Gly Val Gly Val Asp Val Glu Leu Leu Ser Ala Ile Asn Ile Asp
1               5                   10                  15

Asn Glu Thr Phe Ile Glu Arg Asn Phe Thr Gly Asn Glu Val Glu Tyr
            20                  25                  30

Cys Leu Asn Thr Ala His Pro Gln Ala Ser Phe Thr Gly Thr Trp Ser
        35                  40                  45

Ala Lys Glu Ala Val Phe Lys Ala Leu Gly Val Glu Ser Lys Gly Ala
    50                  55                  60

Gly Ala Ser Leu Ile Asp Ile Glu Ile Thr Arg Asp Val Asn Gly Ala
65                  70                  75                  80

Pro Lys Val Ile Leu His Gly Glu Ala Lys Lys Ala Ala Lys Ala
                85                  90                  95

Gly Val Lys Asn Val Asn Ile Ser Ile Ser His Asp Asp Phe Gln Ala
                100                 105                 110

Thr Ala Val Ala Leu Ser Glu Phe
            115                 120
```

(2) INFORMATION FOR SEQ ID NO:2:

(i) SEQUENCE CHARACTERISTICS:
       (A) LENGTH: 121 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO:2:

```
Gly Gly Val Gly Val Asp Val Glu Leu Ile Thr Ser Ile Asn Val Glu
1               5                   10                  15

Asn Asp Thr Phe Ile Glu Arg Asn Phe Thr Pro Gln Glu Ile Glu Tyr
            20                  25                  30

Cys Ser Ala Gln Pro Ser Val Gln Ser Ser Phe Ala Gly Thr Trp Ser
        35                  40                  45

Ala Lys Glu Ala Val Phe Lys Ser Leu Gly Val Lys Ser Leu Gly Gly
    50                  55                  60

Gly Ala Ala Leu Lys Asp Ile Glu Ile Val Arg Val Asn Lys Asn Ala
65                  70                  75                  80

Pro Ala Val Glu Leu His Gly Asn Ala Lys Lys Ala Ala Glu Glu Ala
                85                  90                  95

Gly Val Thr Asp Val Lys Val Ser Ile Ser His Asp Asp Leu Gln Ala
                100                 105                 110
```

```
Val Ala Val Ala Val Ser Thr Lys Lys
        115                 120
```

(2) INFORMATION FOR SEQ ID NO:3:

(i) SEQUENCE CHARACTERISTICS:
        (A) LENGTH: 121 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:3:

```
Asn Ser Lys Ile Gly Val Asp Val Glu His Ile Asp Ser Val Asn Ile
1               5                   10                  15

Glu Asn Glu Thr Phe Val Glu Arg Asn Phe Thr Gln Ser Glu Gln Asp
            20                  25                  30

Tyr Cys Arg Lys Ala Ala Ser Pro Gln Ser Ser Phe Ala Gly Arg Trp
        35                  40                  45

Ser Ala Lys Glu Ala Val Phe Lys Ser Leu Gly Val Ser Ser Lys Gly
    50                  55                  60

Ala Gly Ala Ala Leu Lys Asp Ile Glu Ile Gly Val Asp Ala Asn Gly
65                  70                  75                  80

Ala Pro Val Val Asn Leu His Gly Ala Ala Ala Ala Ala Ala Lys Gln
                85                  90                  95

Ala Gly Val Lys Gln Val Ser Val Ser Ile Ser His Ser Asp Ser Gln
            100                 105                 110

Ala Val Ala Val Ala Val Ser Gln Phe
        115                 120
```

(2) INFORMATION FOR SEQ ID NO:4:

(i) SEQUENCE CHARACTERISTICS:
        (A) LENGTH: 122 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:4:

```
Ser Asn Glu Asn Val Gly Val Asp Val Glu Leu Val Ser Ala Ile Ser
1               5                   10                  15

Ile Asp Asn Glu Thr Phe Ile Glu Arg Asn Phe Thr Asp Thr Glu Arg
            20                  25                  30

Lys Tyr Cys Phe Ala Ala Pro Asn Pro Gln Ala Ser Phe Ala Gly Arg
        35                  40                  45

Trp Ser Ala Lys Glu Ala Val Phe Lys Ser Leu Gly Ile Ser Gly Lys
    50                  55                  60

Gly Ala Ala Ala Pro Leu Lys Asp Ile Glu Ile Ser Ser Glu Ser
65                  70                  75                  80

Gly Ala Pro Glu Val Val Leu His Gly Glu Ala Ala Lys Ala Ala Thr
                85                  90                  95

Thr Ala Gly Val Lys Ser Val Ser Val Ser Ile Ser His Asp Asp Asn
            100                 105                 110

Gln Ser Val Ser Val Ala Leu Ala His Lys
        115                 120
```

(2) INFORMATION FOR SEQ ID NO:5:

(i) SEQUENCE CHARACTERISTICS:
        (A) LENGTH: 130 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:5:

```
Arg Pro Ser Thr Ile Gly Val Asp Thr Val Thr Leu Ser Ser Phe Asn
1               5                   10                  15

Ala His Glu Asn Ala Ile Phe Leu Gln Arg Asn Tyr Thr Glu Arg Glu
            20                  25                  30

Arg Gln Ser Leu Gln Leu Gln Ser His Arg Ser Phe Arg Ser Ala Val
        35                  40                  45

Ala Ser Gly Trp Cys Ala Lys Glu Ala Val Phe Lys Cys Leu Gln Thr
    50                  55                  60

Val Ser Lys Gly Ala Gly Ala Ala Met Ser Glu Ile Glu Ile Val Arg
65                  70                  75                  80

Val Gln Gly Ala Pro Ser Val Leu His Gly Asp Ala Leu Ala Ala Ala
                85                  90                  95

Gln Lys Ala Gly Leu Asp Asn Ile Gln Leu Ser Leu Ser Tyr Gly Asp
            100                 105                 110

Asp Cys Val Val Ala Val Ala Leu Gly Val Arg Lys Trp Cys Leu Trp
        115                 120                 125

Pro Leu
    130
```

(2) INFORMATION FOR SEQ ID NO:6:

(i) SEQUENCE CHARACTERISTICS:
        (A) LENGTH: 129 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:6:

```
Ser Asn His Pro Val Gly Ile Asp Ile Glu Arg Ile Ser Glu Ile Asp
1               5                   10                  15

Ile Lys Ile Ala Glu Gln Phe Phe His Glu Asn Glu Tyr Ile Trp Leu
            20                  25                  30

Gln Ser Lys Ala Gln Asn Ser Gln Val Ser Ser Phe Phe Glu Leu Trp
        35                  40                  45

Thr Ile Lys Glu Ser Tyr Ile Lys Ala Ile Gly Lys Gly Met Tyr Ile
    50                  55                  60

Pro Ile Asn Ser Phe Trp Ile Asp Lys Asn Gln Thr Gln Thr Val Ile
65                  70                  75                  80

Tyr Lys Gln Asn Lys Lys Glu Pro Val Thr Ile Tyr Glu Pro Glu Leu
                85                  90                  95

Phe Glu Gly Tyr Lys Cys Ser Cys Cys Ser Leu Phe Ser Ser Val Thr
            100                 105                 110

Asn Leu Ser Ile Thr Lys Leu Gln Val Gln Glu Leu Cys Asn Leu Phe
        115                 120                 125
```

Leu (2) INFORMATION FOR SEQ ID NO:7:

(i) SEQUENCE CHARACTERISTICS:
        (A) LENGTH: 130 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:7:

```
Ile Val Cys Ala Val Asp Ser Lys Pro Ile Gly Ile Asp Ile Glu Lys
1               5                   10                  15

Met Lys Pro Gly Thr Ile Asp Ile Ala Lys Arg Phe Phe Ser Pro Thr
            20                  25                  30

Glu Tyr Ser Asp Leu Gln Ala Lys His Pro Asp Gln Gln Thr Asp Tyr
            35                  40                  45

Phe Tyr His Leu Trp Ser Met Lys Glu Ser Phe Ile Lys Gln Ala Gly
50                  55                  60

Lys Gly Leu Ser Leu Pro Leu Asp Ser Phe Ser Val Arg Leu Lys Asp
65                  70                  75                  80

Asp Gly His Val Ser Ile Glu Leu Pro Asp Gly His Glu Pro Cys Phe
                85                  90                  95

Ile Arg Thr Tyr Asp Ala Asp Glu Glu Tyr Lys Leu Ala Val Cys Ala
                100                 105                 110

Ala His Pro Asp Phe Cys Asp Gly Ile Glu Met Lys Thr Tyr Glu Glu
            115                 120                 125

Leu Leu
    130
```

(2) INFORMATION FOR SEQ ID NO:8:

(i) SEQUENCE CHARACTERISTICS:
        (A) LENGTH: 130 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:8:

```
Val Ile Gly Ala Phe Asp Ser Gln Pro Ile Gly Ile Asp Ile Glu Lys
1               5                   10                  15

Thr Lys Pro Ile Ser Leu Glu Ile Ala Lys Arg Phe Phe Ser Lys Thr
            20                  25                  30

Glu Tyr Ser Asp Leu Leu Ala Lys Asp Lys Asp Glu Gln Thr Asp Tyr
            35                  40                  45

Phe Tyr His Leu Trp Ser Met Lys Glu Ser Phe Ile Lys Gln Glu Gly
            50                  55                  60

Lys Gly Leu Ser Leu Pro Leu Asp Ser Phe Ser Val Arg Leu His Gln
65                  70                  75                  80

Asp Gly Gln Val Ser Ile Glu Leu Pro Asp Ser His Ser Pro Cys Tyr
                85                  90                  95

Ile Lys Thr Tyr Glu Val Asp Pro Gly Tyr Lys Met Ala Val Cys Ala
                100                 105                 110
```

```
Ala His Pro Asp Phe Pro Glu Asp Ile Thr Met Val Ser Tyr Glu Glu
        115                 120                 125

Leu Leu
    130

(2) INFORMATION FOR SEQ ID NO:9:

(i) SEQUENCE CHARACTERISTICS:
        (A) LENGTH: 107 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:9:

Ser Arg Gln Pro Ile Gly Ile Asp Ile Glu Glu Ile Phe Ser Val Gln
1               5                   10                  15

Thr Ala Arg Glu Leu Thr Asp Asn Ile Ile Thr Pro Ala Glu His Glu
            20                  25                  30

Arg Leu Ala Asp Cys Gly Leu Ala Phe Ser Leu Ala Leu Thr Leu Ala
        35                  40                  45

Phe Ser Ala Lys Glu Ser Ala Phe Lys Ala Ser Glu Ile Gln Thr Asp
    50                  55                  60

Ala Gly Phe Leu Asp Tyr Gln Ile Ile Ser Trp Asn Lys Gln Gln Val
65                  70                  75                  80

Ile Ile His Arg Glu Asn Glu Met Phe Ala Val His Trp Gln Ile Lys
                85                  90                  95

Glu Lys Ile Val Ile Thr Leu Cys Gln His Asp
            100                 105

(2) INFORMATION FOR SEQ ID NO:10:

(i) SEQUENCE CHARACTERISTICS:
        (A) LENGTH: 126 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:10:

Met Ala Ile Leu Gly Leu Gly Thr Asp Ile Val Glu Ile Ala Arg Ile
1               5                   10                  15

Glu Ala Val Ile Ala Arg Ser Gly Asp Arg Leu Ala Arg Arg Val Leu
            20                  25                  30

Ser Asp Asn Glu Trp Ala Ile Trp Lys Thr His His Gln Pro Val Arg
        35                  40                  45

Phe Leu Ala Lys Arg Phe Ala Val Lys Glu Ala Ala Lys Ala Phe
    50                  55                  60

Gly Thr Gly Ile Arg Asn Gly Leu Ala Phe Asn Gln Phe Glu Val Phe
65                  70                  75                  80

Asn Asp Glu Leu Gly Lys Pro Arg Leu Arg Leu Trp Gly Glu Ala Leu
                85                  90                  95

Lys Leu Ala Glu Lys Leu Gly Val Ala Asn Met His Val Thr Leu Ala
            100                 105                 110

Asp Glu Arg His Tyr Ala Cys Ala Thr Val Ile Ile Glu Ser
        115                 120                 125
```

(2) INFORMATION FOR SEQ ID NO:11:

(i) SEQUENCE CHARACTERISTICS:
        (A) LENGTH: 119 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:11:

```
Gly Gly Val Gly Val Asp Val Glu Leu Ile Thr Ser Ile Asn Val Glu
1               5                   10                  15
Asn Asp Thr Phe Ile Glu Arg Asn Phe Thr Pro Gln Glu Ile Glu Tyr
            20                  25                  30
Cys Ser Ala Gln Pro Ser Val Gln Ser Ser Phe Ala Gly Thr Trp Ser
            35                  40                  45
Ala Lys Glu Ala Val Phe Lys Ser Leu Gly Val Lys Ser Leu Gly Gly
        50                  55                  60
Gly Ala Ala Leu Lys Asp Ile Glu Ile Val Arg Val Asn Lys Asn Ala
65                  70                  75                  80
Pro Ala Val Glu Leu His Gly Asn Ala Lys Lys Ala Ala Glu Glu Ala
                85                  90                  95
Gly Val Thr Asp Val Lys Val Ser Ile Ser His Asp Asp Leu Gln Ala
                100                 105                 110
Val Ala Val Ala Val Ser Thr
            115
```

(2) INFORMATION FOR SEQ ID NO:12:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:12:

```
Gly Leu Gly Thr Asp Ile Val Glu Ile
1               5
```

(2) INFORMATION FOR SEQ ID NO:13:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:13:

```
Pro Ile Gly Ile Asp Ile Glu Glu Ile
1               5
```

(2) INFORMATION FOR SEQ ID NO:14:

(i) SEQUENCE CHARACTERISTICS:
        (A) LENGTH: 9 amino acids
        (B) TYPE: amino acid
        (D) TOPOLOGY: linear

```
        (ii) MOLECULE TYPE: peptide (v) FRAGMENT TYPE: internal (xi) SEQUENCE DESCRIPTION: SEQ ID NO:14:

Pro Ile Gly Val Asp Ile Glu Glu Ile
1               5

(2) INFORMATION FOR SEQ ID NO:15:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:15:

Arg Ile Gly Ile Asp Ile Glu Lys Ile
1               5

(2) INFORMATION FOR SEQ ID NO:16:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:16:

Arg Val Gly Val Asp Ile Glu Lys Ile
1               5

(2) INFORMATION FOR SEQ ID NO:17:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:17:

Pro Ile Gly Ile Asp Ile Glu Lys Thr
1               5

(2) INFORMATION FOR SEQ ID NO:18:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:18:

Pro Val Gly Ile Asp Ile Glu Glu Ile
1               5
```

(2) INFORMATION FOR SEQ ID NO:19:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:19:

Pro Val Gly Ile Asp Ile Glu Arg Ile
1           5

(2) INFORMATION FOR SEQ ID NO:20:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:20:

Pro Ile Gly Ile Asp Ile Glu Lys Met
1           5

(2) INFORMATION FOR SEQ ID NO:21:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:21:

Gly Val Gly Ile Asp Ala Glu Pro His
1           5

(2) INFORMATION FOR SEQ ID NO:22:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:22:

Glu Val Gly Cys Asp Ile Glu Val Ile
1           5

(2) INFORMATION FOR SEQ ID NO:23:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:23:

Gln Ile Gly Ile Asp Leu Glu Tyr Leu
1               5

(2) INFORMATION FOR SEQ ID NO:24:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:24:

Glu Ile Gly Val Asp Leu Gln Ile Met
1               5

(2) INFORMATION FOR SEQ ID NO:25:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:25:

Asp Val Gly Ile Asp Ile Ala Ser Pro
1               5

(2) INFORMATION FOR SEQ ID NO:26:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:26:

Lys Val Gly Val Asp Val Met Arg Leu
1               5

(2) INFORMATION FOR SEQ ID NO:27:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:27:

Ala Val Gly Ile Asp Ile Glu Phe Pro
1               5

(2) INFORMATION FOR SEQ ID NO:28:

(i) SEQUENCE CHARACTERISTICS:
        (A) LENGTH: 9 amino acids
        (B) TYPE: amino acid (D) TOPOLOGY: linear (ii) MOLECULE TYPE: peptide (v) FRAGMENT TYPE: internal (xi) SEQUENCE DESCRIPTION: SEQ ID NO:28:

Asn Ile Gly Val Asp Ile Val Glu Cys
1               5

(2) INFORMATION FOR SEQ ID NO:29:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:29:

Thr Ile Gly Val Asp Thr Val Thr Leu
1               5

(2) INFORMATION FOR SEQ ID NO:30:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:30:

Asn Val Gly Val Asp Val Glu Leu Val
1               5

(2) INFORMATION FOR SEQ ID NO:31:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:31:

Gly Val Gly Val Asp Val Glu Leu Leu
1               5

(2) INFORMATION FOR SEQ ID NO:32:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:32:

Lys Ile Gly Val Asp Val Glu His Ile
1               5

(2) INFORMATION FOR SEQ ID NO:33:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:33:

```
Gly Val Gly Val Asp Val Glu Leu Ile
1               5
```

(2) INFORMATION FOR SEQ ID NO:34:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:34:

```
Phe Ala Val Lys Glu Ala Ala Lys Ala Phe Gly
1               5                   10
```

(2) INFORMATION FOR SEQ ID NO:35:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:35:

```
Phe Ser Ala Lys Glu Ser Ala Phe Lys Ala Ser Glu
1               5                   10
```

(2) INFORMATION FOR SEQ ID NO:36:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:36:

```
Phe Ser Ala Lys Glu Ser Ala Phe Lys Ala Ser Glu
1               5                   10
```

(2) INFORMATION FOR SEQ ID NO:37:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:37:

Phe Ser Ala Lys Glu Ser Val Tyr Lys Ala Phe Gln
1               5                   10

(2) INFORMATION FOR SEQ ID NO:38:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:38:

Phe Ser Ala Lys Glu Ser Val Tyr Lys Ala Phe Gln
1               5                   10

(2) INFORMATION FOR SEQ ID NO:39:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:39:

Trp Ser Met Lys Glu Ser Phe Ile Lys Gln Glu Gly
1               5                   10

(2) INFORMATION FOR SEQ ID NO:40:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:40:

Trp Ser Met Lys Glu Ala Phe Ile Lys Leu Thr Gly
1               5                   10

(2) INFORMATION FOR SEQ ID NO:41:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:41:

Trp Thr Ile Lys Glu Ser Tyr Ile Lys Ala Ile Gly
1               5                   10

(2) INFORMATION FOR SEQ ID NO:42:

(i) SEQUENCE CHARACTERISTICS:
        (A) LENGTH: 12 amino acids

```
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:42:

Trp Ser Met Lys Glu Ser Phe Ile Lys Gln Ala Gly
1               5                   10

(2) INFORMATION FOR SEQ ID NO:43:

(i) SEQUENCE CHARACTERISTICS:
          (A) LENGTH: 12 amino acids
          (B) TYPE: amino acid
          (D) TOPOLOGY: linear (ii) MOLECULE TYPE: peptide (v) FRAGMENT TYPE: internal (xi) SEQUENCE DESCRIPTION: SEQ ID NO:43:

Phe Cys Val Lys Glu Ala Val Phe Lys Ala Trp Tyr
1               5                   10

(2) INFORMATION FOR SEQ ID NO:44:

(i) SEQUENCE CHARACTERISTICS:
          (A) LENGTH: 12 amino acids
          (B) TYPE: amino acid
          (D) TOPOLOGY: linear (ii) MOLECULE TYPE: peptide (v) FRAGMENT TYPE: internal (xi) SEQUENCE DESCRIPTION: SEQ ID NO:44:

Trp Thr Arg Lys Glu Ala Ile Val Lys Gln Arg Gly
1               5                   10

(2) INFORMATION FOR SEQ ID NO:45:

(i) SEQUENCE CHARACTERISTICS:
          (A) LENGTH: 12 amino acids
          (B) TYPE: amino acid
          (D) TOPOLOGY: linear (ii) MOLECULE TYPE: peptide (v) FRAGMENT TYPE: internal (xi) SEQUENCE DESCRIPTION: SEQ ID NO:45:

Trp Thr Cys Lys Glu Ala Tyr Leu Lys Ala Thr Gly
1               5                   10

(2) INFORMATION FOR SEQ ID NO:46:

(i) SEQUENCE CHARACTERISTICS:
          (A) LENGTH: 12 amino acids
          (B) TYPE: amino acid
          (D) TOPOLOGY: linear (ii) MOLECULE TYPE: peptide (v) FRAGMENT TYPE: internal (xi) SEQUENCE DESCRIPTION: SEQ ID NO:46:

Trp Thr Ala Lys Glu Ala Phe Leu Lys Ala Thr Gly
1               5                   10
```

(2) INFORMATION FOR SEQ ID NO:47:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:47:

Trp Ser Leu Lys Glu Ser Tyr Thr Lys Phe Thr Gly
1               5                   10

(2) INFORMATION FOR SEQ ID NO:48:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:48:

Trp Cys Leu Lys Glu Ala Ile Leu Lys Ala Thr Gly
1               5                   10

(2) INFORMATION FOR SEQ ID NO:49:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:49:

Trp Cys Leu Arg Glu Ala Val Leu Lys Ser Gln Gly
1               5                   10

(2) INFORMATION FOR SEQ ID NO:50:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:50:

Trp Thr Cys Lys Glu Ala Ile Leu Lys Ala Leu Gly
1               5                   10

(2) INFORMATION FOR SEQ ID NO:51:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:51:

Trp Cys Ala Lys Glu Ala Val Phe Lys Cys Leu Gln
1               5                   10

(2) INFORMATION FOR SEQ ID NO:52:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:52:

Trp Ser Ala Lys Glu Ala Val Phe Lys Ser Leu Gly
1               5                   10

(2) INFORMATION FOR SEQ ID NO:53:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:53:

Trp Ser Ala Lys Glu Ala Val Phe Lys Ala Leu Gly
1               5                   10

(2) INFORMATION FOR SEQ ID NO:54:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:54:

Trp Ser Ala Lys Glu Ala Val Phe Lys Ser Leu Gly
1               5                   10

(2) INFORMATION FOR SEQ ID NO:55:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:55:

Trp Ser Ala Lys Glu Ala Val Phe Lys Ser Leu Gly
1               5                   10

(2) INFORMATION FOR SEQ ID NO:56:

(i) SEQUENCE CHARACTERISTICS:

(A) LENGTH: 112 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:56:

```
Met Pro Leu Thr Pro Asn Asp Lys Ile Asp Arg Lys Ala Leu Pro Glu
1               5                  10                  15

Pro Asp Leu Thr Ala Asn Gln Ser Gln Ala Ala Tyr His Pro Pro Arg
            20                  25                  30

Thr Glu Thr Glu Ser Ile Leu Val Ser Ile Trp Gln Asn Val Leu Gly
        35                  40                  45

Ile Glu Lys Ile Gly Ile Arg Asp Asn Phe Tyr Ser Leu Gly Gly Asp
 50                  55                  60

Ser Ile Gln Ala Ile Gln Val Val Ala Arg Leu His Ser Tyr Gln Leu
 65                  70                  75                  80

Lys Leu Glu Thr Lys Asp Leu Leu Asn Tyr Pro Thr Ile Glu Gln Val
                85                  90                  95

Ala Leu Phe Val Lys Ser Thr Thr Arg Ser His His His His His His
                100                 105                 110
```

(2) INFORMATION FOR SEQ ID NO:57:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 2
        (C) OTHER INFORMATION: /note= "Xaa is any amino acid"

(ix) FEATURE:
        (A) NAME/KEY: Modified-site
        (B) LOCATION: 4-5
        (C) OTHER INFORMATION: /note= "Xaa is any amino acid"

(xi) SEQUENCE DESCRIPTION: SEQ ID NO:57:

```
Gly Xaa Asp Xaa Xaa Glu
1               5
```

(2) INFORMATION FOR SEQ ID NO:58:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 6-8
        (C) OTHER INFORMATION: /note= "Xaa is any amino acid"

(ix) FEATURE:
        (A) NAME/KEY: Modified-site
        (B) LOCATION: 10-11
        (C) OTHER INFORMATION: /note= "Xaa is any amino acid"

(xi) SEQUENCE DESCRIPTION: SEQ ID NO:58:

Trp Ser Ala Lys Glu Xaa Xaa Xaa Lys Xaa Xaa Gly
1               5                   10

(2) INFORMATION FOR SEQ ID NO:59:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (v) FRAGMENT TYPE: internal (ix) FEATURE:
            (A) NAME/KEY: Modified-site
            (B) LOCATION: 1
            (C) OTHER INFORMATION: /note= "Xaa may be either Phe or Trp"

(ix) FEATURE:
            (A) NAME/KEY: Modified-site
            (B) LOCATION: 2-3
            (C) OTHER INFORMATION: /note= "Xaa is any amino acid"

(ix) FEATURE:
            (A) NAME/KEY: Modified-site
            (B) LOCATION: 4
            (C) OTHER INFORMATION: /note= "Xaa may be either Lys or Arg"

(ix) FEATURE:
            (A) NAME/KEY: Modified-site
            (B) LOCATION: 6
            (C) OTHER INFORMATION: /note= "Xaa may be either Ser or Ala"

(ix) FEATURE:
            (A) NAME/KEY: Modified-site
            (B) LOCATION: 7-8
            (C) OTHER INFORMATION: /note= "Xaa is any amino acid"

(xi) SEQUENCE DESCRIPTION: SEQ ID NO:59:

Xaa Xaa Xaa Xaa Glu Xaa Xaa Xaa Lys
1               5

(2) INFORMATION FOR SEQ ID NO:60:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:60:

Gly Thr Asp Ile Val Glu Ile Ala Arg Ile
1               5                   10

(2) INFORMATION FOR SEQ ID NO:61:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:61:

```
Gly Ile Asp Ile Glu Glu Ile Phe Ser Val
1               5                   10
```

(2) INFORMATION FOR SEQ ID NO:62:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:62:

```
Gly Ile Asp Ile Glu Lys Thr Lys Pro Ile
1               5                   10
```

(2) INFORMATION FOR SEQ ID NO:63:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:63:

```
Gly Ile Asp Ile Glu Arg Ile Ser Glu Ile
1               5                   10
```

(2) INFORMATION FOR SEQ ID NO:64:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:64:

```
Gly Val Asp Val Glu Leu Ile Thr Ser Ile
1               5                   10
```

(2) INFORMATION FOR SEQ ID NO:65:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:65:

```
Phe Ala Val Lys Glu Ala Ala Ala Lys Ala Phe Gly
1               5                   10
```

(2) INFORMATION FOR SEQ ID NO:66:

(i) SEQUENCE CHARACTERISTICS:
        (A) LENGTH: 12 amino acids
        (B) TYPE: amino acid
        (D) TOPOLOGY: linear

```
    (ii) MOLECULE TYPE: peptide (v) FRAGMENT TYPE: internal (xi) SEQUENCE DESCRIPTION: SEQ ID NO:66:

Phe Ser Ala Lys Glu Ser Ala Phe Lys Ala Ser Glu
1               5                   10

(2) INFORMATION FOR SEQ ID NO:67:

(i) SEQUENCE CHARACTERISTICS:
         (A) LENGTH: 12 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO:67:

Trp Ser Met Lys Glu Ser Phe Ile Lys Gln Glu Gly
1               5                   10

(2) INFORMATION FOR SEQ ID NO:68:

(i) SEQUENCE CHARACTERISTICS:
         (A) LENGTH: 12 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO:68:

Trp Thr Ile Lys Glu Ser Tyr Ile Lys Ala Ile Gly
1               5                   10

(2) INFORMATION FOR SEQ ID NO:69:

(i) SEQUENCE CHARACTERISTICS:
         (A) LENGTH: 12 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO:69:

Trp Ser Ala Lys Glu Ala Val Phe Lys Ser Leu Gly
1               5                   10

(2) INFORMATION FOR SEQ ID NO:70:

(i) SEQUENCE CHARACTERISTICS:
         (A) LENGTH: 16 amino acids
         (B) TYPE: amino acid
         (D) TOPOLOGY: linear (ii) MOLECULE TYPE: peptide (v) FRAGMENT TYPE: internal (ix) FEATURE:
         (A) NAME/KEY: Modified-site
         (B) LOCATION: 2
         (C) OTHER INFORMATION: /note= "Xaa may be Asn or Asp"

(ix) FEATURE:
         (A) NAME/KEY: Modified-site
```

```
      (B) LOCATION: 5
      (C) OTHER INFORMATION: /note= "Xaa is any amino acid"

(ix) FEATURE:
      (A) NAME/KEY: Modified-site
      (B) LOCATION: 6
      (C) OTHER INFORMATION: /note= "Xaa may be Leu or Ile"

(ix) FEATURE:
      (A) NAME/KEY: Modified-site
      (B) LOCATION: 9
      (C) OTHER INFORMATION: /note= "Xaa may be His or Asp"

(ix) FEATURE:
      (A) NAME/KEY: Modified-site
      (B) LOCATION: 11
      (C) OTHER INFORMATION: /note= "Xaa may be Leu or Ile"

(ix) FEATURE:
      (A) NAME/KEY: Modified-site
      (B) LOCATION: 12
      (C) OTHER INFORMATION: /note= "Xaa is any amino acid"

(ix) FEATURE:
      (A) NAME/KEY: Modified-site
      (B) LOCATION: 13
      (C) OTHER INFORMATION: /note= "Xaa may be Ala, Gly or Cys"

(ix) FEATURE:
      (A) NAME/KEY: Modified-site
      (B) LOCATION: 14-15
      (C) OTHER INFORMATION: /note= "Xaa is any amino acid"

(ix) FEATURE:
      (A) NAME/KEY: Modified-site
      (B) LOCATION: 16
      (C) OTHER INFORMATION: /note= "Xaa may be Leu, Val or Met"

(xi) SEQUENCE DESCRIPTION: SEQ ID NO:70:

Asp Xaa Phe Phe Xaa Xaa Gly Gly Xaa Ser Xaa Xaa Xaa Xaa Xaa
1               5                   10                  15

Xaa (2) INFORMATION FOR SEQ ID NO:71:

(i) SEQUENCE CHARACTERISTICS:
      (A) LENGTH: 7 amino acids
      (B) TYPE: amino acid
      (D) TOPOLOGY: linear (ii) MOLECULE TYPE: peptide (v) FRAGMENT TYPE: internal (ix) FEATURE:
      (A) NAME/KEY: Modified-site
      (B) LOCATION: 1
      (C) OTHER INFORMATION: /note= "Xaa may be Leu or Val"

(ix) FEATURE:
      (A) NAME/KEY: Modified-site
      (B) LOCATION: 2
      (C) OTHER INFORMATION: /note= "Xaa may be Gly or Leu"

(ix) FEATURE:
      (A) NAME/KEY: Modified-site
      (B) LOCATION: 3
      (C) OTHER INFORMATION: /note= "Xaa may be Gly, Ala, Phe or
          Tyr"

(ix) FEATURE:
      (A) NAME/KEY: Modified-site
      (B) LOCATION: 4
      (C) OTHER INFORMATION: /note= "Xaa may be Asp, His, Lys or
          Glu"
```

```
    (ix) FEATURE:
          (A) NAME/KEY: Modified-site
          (B) LOCATION: 6
          (C) OTHER INFORMATION: /note= "Xaa may be Leu or Gln"

(ix) FEATURE:
          (A) NAME/KEY: Modified-site
          (B) LOCATION: 7
          (C) OTHER INFORMATION: /note= "Xaa may be Asp or Ala or Gly"

(xi) SEQUENCE DESCRIPTION: SEQ ID NO:71:

Xaa Xaa Xaa Xaa Ser Xaa Xaa
1               5

(2) INFORMATION FOR SEQ ID NO:72:

(i) SEQUENCE CHARACTERISTICS:
          (A) LENGTH: 40 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:72:

TGTACCTCAG ACCATATGGC AATATTAGGT TTAGGCACGG                              40

(2) INFORMATION FOR SEQ ID NO:73:

(i) SEQUENCE CHARACTERISTICS:
          (A) LENGTH: 40 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:73:

TGATGTCAGT CAAGCTTAAC TTTCAATAAT TACCGTGGCA                              40

(2) INFORMATION FOR SEQ ID NO:74:

(i) SEQUENCE CHARACTERISTICS:
          (A) LENGTH: 25 amino acids
          (B) TYPE: amino acid
          (D) TOPOLOGY: linear (ii) MOLECULE TYPE: peptide (v) FRAGMENT TYPE: internal (xi) SEQUENCE DESCRIPTION: SEQ ID NO:74:

Ala Ile Leu Gly Leu Gly Thr Asp Ile Val Glu Ile Ala Arg Ile Glu
1               5                   10                  15

Ala Val Ile Ala Arg Ser Gly Asp Arg
            20                  25

(2) INFORMATION FOR SEQ ID NO:75:

(i) SEQUENCE CHARACTERISTICS:
          (A) LENGTH: 53 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:75:

ATTATATCCA TGGGTTCCTC CGTTTCCAAC ATGGTCGATA TGAAAACTAC GCA               53
```

-continued (2) INFORMATION FOR SEQ ID NO:76:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:76:

GATGTCAAGC TTATTAATCG TGTTGGCACA GCGTTAT     37

(2) INFORMATION FOR SEQ ID NO:77:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:77:

ATTATATCCA TGGGTTACCG GATAGTTCTG GGGAAAGTT     39

(2) INFORMATION FOR SEQ ID NO:78:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:78:

TGATGTCAAG CTTATCAGTT AACTGAATCG ATCCATTG     38